US012203100B2

(12) United States Patent
Whitehead et al.

(10) Patent No.: US 12,203,100 B2
(45) Date of Patent: *Jan. 21, 2025

(54) DEVELOPMENT OF DENGUE VIRUS VACCINE COMPONENTS

(71) Applicant: The Government of the USA as represented by the Secretary, Dept. of Health and Human Services, Bethesda, MD (US)

(72) Inventors: Stephen S. Whitehead, Bethesda, MD (US); Joseph E. Blaney, Gettysburg, PA (US); Brian R. Murphy, Bethesda, MD (US); Ching-Juh Lai, Bethesda, MD (US)

(73) Assignee: The Government of the USA as represented by the Secretary, Dept. of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/355,265

(22) Filed: Jul. 19, 2023

(65) Prior Publication Data

US 2024/0084269 A1   Mar. 14, 2024

Related U.S. Application Data

(60) Continuation of application No. 17/724,037, filed on Apr. 19, 2022, now Pat. No. 11,746,335, which is a continuation of application No. 16/912,359, filed on Jun. 25, 2020, now Pat. No. 11,332,722, which is a continuation of application No. 16/173,217, filed on Oct. 29, 2018, now Pat. No. 10,724,007, which is a continuation of application No. 14/742,533, filed on Jun. 17, 2015, now Pat. No. 10,160,957, which is a continuation of application No. 13/692,557, filed on Dec. 3, 2012, now Pat. No. 9,090,873, which is a division of application No. 12/376,756, filed as application No. PCT/US2007/076004 on Aug. 15, 2007, now Pat. No. 8,337,860.

(60) Provisional application No. 60/837,723, filed on Aug. 15, 2006.

(51) Int. Cl.
| | |
|---|---|
| *C12N 7/04* | (2006.01) |
| *A61K 39/00* | (2006.01) |
| *C07K 14/005* | (2006.01) |
| *C07K 14/18* | (2006.01) |
| *C12N 7/00* | (2006.01) |

(52) U.S. Cl.
CPC ............ *C12N 7/045* (2013.01); *C07K 14/005* (2013.01); *C07K 14/1825* (2013.01); *C12N 7/00* (2013.01); *A61K 2039/5254* (2013.01); *C12N 2770/24122* (2013.01); *C12N 2770/24162* (2013.01); *Y02A 50/30* (2018.01)

(58) Field of Classification Search
CPC ............ C12N 7/00; C12N 2770/24134; C12N 2770/24161; C12N 2770/24162; C12N 2770/24122; C12N 2770/24171; C12N 2770/24121; C12N 7/045; C12N 15/86; C12N 2770/24143; C12N 2770/24151; A61K 2039/5254; A61K 39/12; A61K 2039/53; C07K 14/005; C07K 14/1825
See application file for complete search history.

(56) References Cited

U.S. PATENT DOCUMENTS

| | | | |
|---|---|---|---|
| 7,517,531 B2 | 4/2009 | Whitehead et al. |
| 7,851,194 B2 | 12/2010 | Markoff et al. |
| 8,075,903 B2 | 12/2011 | Whitehead et al. |
| 8,337,860 B2 | 12/2012 | Whitehead et al. |
| 9,090,873 B2 | 7/2015 | Whitehead et al. |
| RE46,042 E | 6/2016 | Whitehead et al. |
| 9,783,787 B2 | 10/2017 | Whitehead et al. |
| RE46,631 E | 12/2017 | Whitehead et al. |

(Continued)

FOREIGN PATENT DOCUMENTS

| | | |
|---|---|---|
| WO | WO 2008/022196 | 2/2008 |
| WO | WO 03/092592 | 11/2013 |

OTHER PUBLICATIONS

Whitehead SS, Falgout B, Hanley KA, Blaney JE Jr, Markoff L, Murphy Br. A live, attenuated dengue virus type 1 vaccine candidate with a 30-nucleotide deletion in the 3' untranslated region is highly attenuated and immunogenic in monkeys. J Virol. Jan. 2003;77(2):1653-7. (Year: 2003).*

Alvarez et al., "Role of RNA structures present at the 3' UTR of dengue virus on translation, RNA synthesis, and viral replication," *Virology*, vol. 339, pp. 200-212, 2005.

Blaney et al., "Dengue virus type 3 vaccine candidates generated by introduction of deletions in the 3' untranslated region (3'-UTR) or by exchange of the DENV-3 3'-UTR with that of DENV-4," *Vaccine*, vol. 26, pp. 817-828, 2008.

(Continued)

*Primary Examiner* — Rachel B Gill
(74) *Attorney, Agent, or Firm* — Klarquist Sparkman, LLP

(57) ABSTRACT

The invention is related to a dengue virus or chimeric dengue virus that contains a mutation in the 3' untranslated region (3'-UTR) comprising a Δ30 mutation that removes the TL-2 homologous structure in each of the dengue virus serotypes 1, 2, 3, and 4, and nucleotides additional to the Δ30 mutation deleted from the 3'-UTR that removes sequence in the 5' direction as far as the 5' boundary of the TL-3 homologous structure in each of the dengue serotypes 1, 2, 3, and 4, or a replacement of the 3'-UTR of a dengue virus of a first serotype with the 3'-UTR of a dengue virus of a second serotype, optionally containing the Δ30 mutation and nucleotides additional to the Δ30 mutation deleted from the 3'-UTR; and immunogenic compositions, methods of inducing an immune response, and methods of producing a dengue virus or chimeric dengue virus.

3 Claims, 22 Drawing Sheets

Specification includes a Sequence Listing.

(56) References Cited

U.S. PATENT DOCUMENTS

RE46,641 E    12/2017  Whitehead et al.
2018/0010099 A1  1/2018  Whitehead et al.

OTHER PUBLICATIONS

Blaney Jr., et al., "Development of a Live Attenuated Dengue Virus Vaccine Using Reverse Genetics," *Viral Immunology*, vol. 19, No. 1, pp. 10-32, 2006.
Blaney Jr., et al., "Genetically Modified, Live Attenuated Dengue Virus Type 3 Vaccine Candidates," *Am. J. Trap. Med. Hyg.*, vol. 71, pp. 811-821, 2004.
Durbin et al., "rDEN2/4Δ30(ME), A Live Attenuated Chimeric Dengue Serotype 2 Vaccine Is Safe and Highly Immunogenic in Healthy Dengue-Naive Adults," *Human Vaccines*, vol. 2, No. 6, pp. 255-260, 2006.
International Search Report dated Jan. 13, 2009 for PCT/US2007/076004.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," *Journal of Virology*, vol. 70, No. 5, pp. 3930-3937, 1996.
Proutski et al., "Secondary structure of the 3' untranslated region of flaviviruses: similarities and differences," *Nucleic Acids Research*, vol. 25, No. 6, pp. 1194-1202, 1997.
Whitehead et al., "Substitution of the structural genes of dengue virus type 4 with those of type 2 results in chimeric vaccine candidates which are attenuated for mosquitoes, mice, and rhesus monkeys," *Vaccine*, vol. 21, pp. 4307-4316, 2003.
Worobey et al., "Widespread intra-serotype recombination in natural populations of dengue virus," *Proc. Natl. Acad. Sci.*, vol. 96, pp. 7352-7357, 1999.
Yu et al., "The topology of bulges in the long stem of the flavivirus 3' stem-loop is a major determinant of RNA replication competence." *Journal of Virology*, vol. 79, pp. 2309-2324, 2005.
Zeng et al., "Identification of specific nucleotide sequences within the conserved 3'-SL in the dengue type 2 virus genome required for replication," *Journal of Virology*, vol. 72, pp. 7510-7522, 1988.
Zhou et al., "Comparative analysis reveals no consistent association between the secondary structure of the 3'-untranslated region of dengue viruses and disease syndrome," *Journal of General Virology*, vol. 87, pp. 2595-2603, 2006.

* cited by examiner

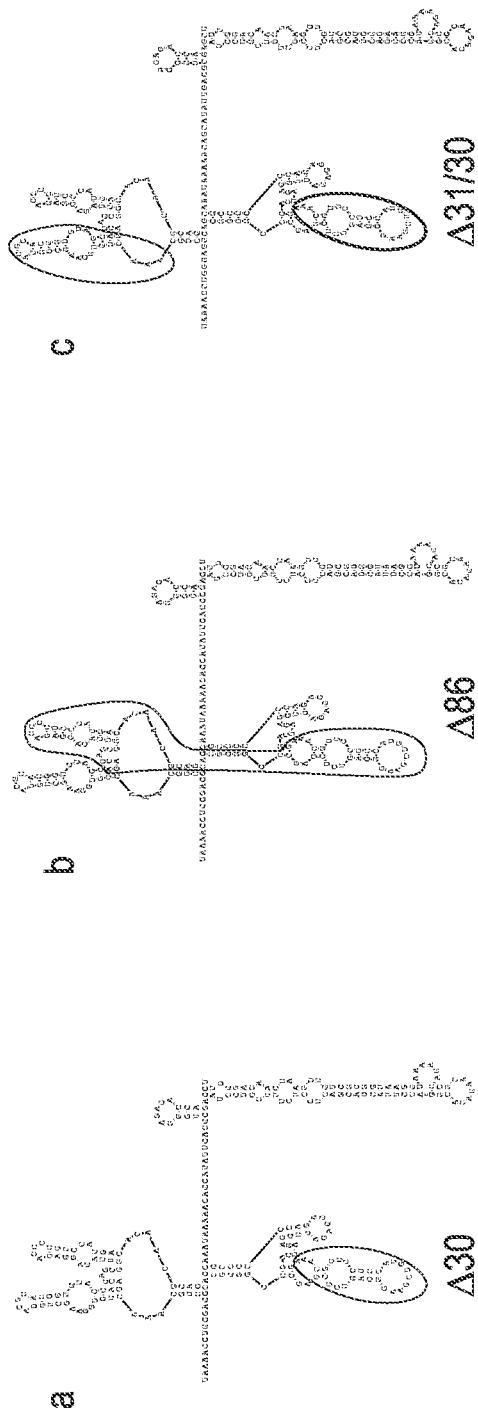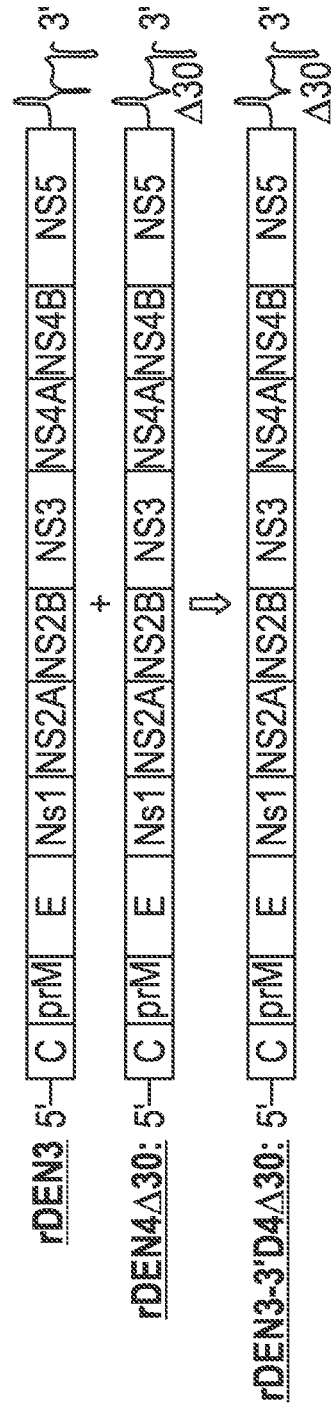
Figure 1

DEN4Δ30
ΔG=-80.4
(mfold v3.2: 1 0 4, P 82 0 15, P 137

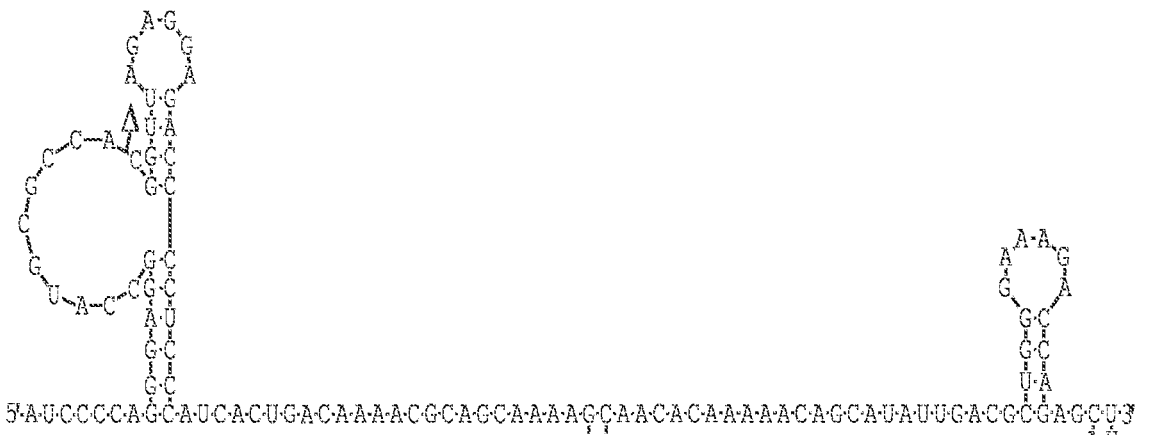
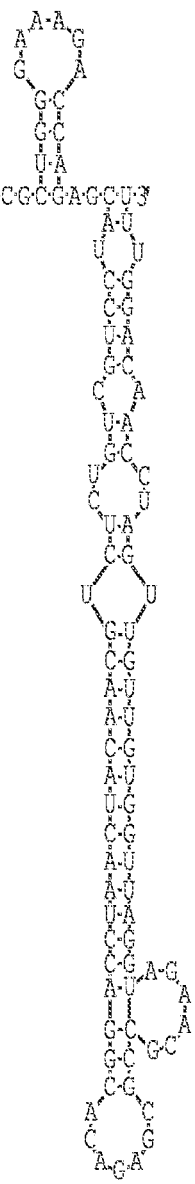
DEN4Δ30/31
ΔG=-64.9
(mfold v3.2: 1 0 4, P 51 0 15, P 106 0 20)
Figure 13

SEQUENCE LISTING

```
Sequence total quantity: 33
SEQ ID NO: 1            moltype = RNA  length = 276
FEATURE                 Location/Qualifiers
source                  1..276
                        mol_type = unassigned RNA
                        organism = Dengue virus
SEQUENCE: 1
taaaacctgg gaggctgcaa actgtggaag ctgtacgcac ggtgtagcag actagcggtt  60
agaggagacc cctcccatga cacaacgcag cagcggggcc cgagctctga gggaagctgt  120
acctccttgc aaaggactag aggttagagg agacccccg caaataaaaa cagcatattg  180
acgctgggag agaccagaga tcctgctgtc tcctcagcat cattccaggc acagaacgcc  240
agaaaatgga atggtgctgt tgaatcaaca ggttct                            276

SEQ ID NO: 2            moltype = RNA  length = 278
FEATURE                 Location/Qualifiers
source                  1..278
                        mol_type = unassigned RNA
                        organism = Dengue virus
SEQUENCE: 2
taaaaacccg ggaggctgca aaccatggaa gctgtacgca tggggtagca gactagtggt  60
tagaggagac ccctcccaag acacaacgca gcagcggggc ccaacaccag gggaagctgt  120
accctggtgg taaggactag aggttagagg agacccccg cacaacaaca aacagcatat  180
tgacgctggg agagaccaga gatcctgctg tctctacagc atcattccag gcacagaacg  240
ccagaaaatg gaatggtgct gttgaatcaa caggttct                          278

SEQ ID NO: 3            moltype = RNA  length = 281
FEATURE                 Location/Qualifiers
source                  1..281
                        mol_type = unassigned RNA
                        organism = Dengue virus
SEQUENCE: 3
taaaaaatcc gggaggccac aaaccatgga agctgtacgc atggcgtagt ggactagcgg  60
ttagaggaga cccctcccct acagatcgca gcaacaatgg gggcccaagg tgagatgaag  120
ctgtagtctc actggaagga ctagaggtta gaggagaccc ccccaaaaca aaaaacagca  180
tattgacgct gggaaagacc agagatcctg ctgtctcctc agcatcattc caggcacagg  240
acgccagaaa atggaatggt gctgttgaat caacaggttc t                      281

SEQ ID NO: 4            moltype = RNA  length = 276
FEATURE                 Location/Qualifiers
source                  1..276
                        mol_type = unassigned RNA
                        organism = Dengue virus
SEQUENCE: 4
taaaacctgg gaggctgcaa actgtggaag ctgtacgcac ggtgtagcag actagcggtt  60
agaggagacc cctcccatga cacaacgcag cagcggggcc cgagctctga gggaagctgt  120
acctccttgc aaaggactag aggttagagg agacccccg caaataaaaa cagcatattg  180
acgctgggag agaccagaga tcctgctgtc tcctcagcat cattccaggc acagaacgcc  240
agaaaatgga atggtgctgt tgaatcaaca ggttct                            276

SEQ ID NO: 5            moltype = RNA  length = 281
FEATURE                 Location/Qualifiers
source                  1..281
                        mol_type = unassigned RNA
                        organism = Dengue virus
SEQUENCE: 5
atccccaggg aggccatgcg ccacggaagc tgtacgcgtg gcatattgga ctagcggtta  60
gaggagaccc ctcccatcac tgacaaaacg cagcaaaagg gggcccgaag ccaggaggaa  120
gctgtactcc tggtggaagg actagaggtt agaggagacc cccccaacac aaaaacagca  180
tattgacgct gggaaagacc agagatcctg ctgtctctgc aacatcaatc caggcacaga  240
gcgccgcaag atggattggt gttgttgatc caacaggttc t                      281

SEQ ID NO: 6            moltype = RNA  length = 248
FEATURE                 Location/Qualifiers
misc_feature            1..248
                        note = Dengue virus construct
source                  1..248
                        mol_type = other RNA
                        organism = synthetic construct
SEQUENCE: 6
taaaaacccg ggaggctgca aaccatggaa gctgtacgca tggggtagca gactagtggt  60
tagaggagac ccctcccaag acacaacgca gcagcggggc ccaagactag aggttagagg  120
agacccccg cacaacaaca aacagcatat tgacgctggg agagaccaga gatcctgctg  180
tctctacagc atcattccag gcacagaacg ccagaaaatg gaatggtgct gttgaatcaa  240
caggttct                                                           248
```

-continued

```
SEQ ID NO: 7            moltype = RNA  length = 251
FEATURE                 Location/Qualifiers
misc_feature            1..251
                        note = Dengue virus construct
source                  1..251
                        mol_type = other RNA
                        organism = synthetic construct
SEQUENCE: 7
taaaaaatcc gggaggccac aaaccatgga agctgtacgc atggcgtagt ggactagcgg  60
ttagaggaga cccctccctt acagatcgca gcaacaatgg gggcccaaga ctagaggtta  120
gaggagaccc ccccaaaaca aaaaacagca tattgacgct gggaaagacc agagatcctg  180
ctgtctcctc agcatcattc caggcacagg acgccagaaa atggaatggt gctgttgaat  240
caacaggttc t                                                        251

SEQ ID NO: 8            moltype = RNA  length = 245
FEATURE                 Location/Qualifiers
misc_feature            1..245
                        note = Dengue virus construct
source                  1..245
                        mol_type = other RNA
                        organism = synthetic construct
SEQUENCE: 8
taaaacctgg gaggctgcaa actgtggaag ctgtacgcac ggtgtagcag actagcggtt  60
agaggagacc cctcccatga cacaacgcag cagcggggcc caagactaga ggttagagga  120
gaccccccgc aaataaaaac agcatattga cgctgggaga gaccagagat cctgctgtct  180
cctcagcatc attccaggca cagaacgcca gaaaatggaa tggtgctgtt gaatcaacag  240
gttct                                                               245

SEQ ID NO: 9            moltype = RNA  length = 250
FEATURE                 Location/Qualifiers
misc_feature            1..250
                        note = Dengue virus construct
source                  1..250
                        mol_type = other RNA
                        organism = synthetic construct
SEQUENCE: 9
atccccaggg aggccatgcg ccacggaagc tgtacgcgtg gcatattgga ctagcggtta  60
gaggagaccc ctcccatcac tgacaaaacg cagcaaaagg gggcccaaga ctagaggtta  120
gaggagaccc ccccaacaca aaaacagcat attgacgctg ggaaagacca gagatcctgc  180
tgtctctgca acatcaatcc aggcacagag cgccgcaaga tggattggtg ttgttgatcc  240
aacaggttct                                                          250

SEQ ID NO: 10           moltype = RNA  length = 217
FEATURE                 Location/Qualifiers
misc_feature            1..217
                        note = Dengue virus construct
source                  1..217
                        mol_type = other RNA
                        organism = synthetic construct
SEQUENCE: 10
taaaaacccg ggaggctgca actagtggtt agaggagacc cctcccaaga cacaacgcag  60
cagcggggcc caagactaga ggttagagga gacccccccgc acaacaacaa acagcatatt  120
gacgctggga gagaccagag atcctgctgt ctctacagca tcattccagg cacagaacgc  180
cagaaaatgg aatggtgctg ttgaatcaac aggttct                            217

SEQ ID NO: 11           moltype = RNA  length = 220
FEATURE                 Location/Qualifiers
misc_feature            1..220
                        note = Dengue virus construct
source                  1..220
                        mol_type = other RNA
                        organism = synthetic construct
SEQUENCE: 11
taaaaaatcc gggaggccac aaatagcggt tagaggagac ccctccctta cagatcgcag  60
caacaatggg ggcccaagac tagaggttag aggagacccc cccaaaacaa aaaacagcat  120
attgacgctg ggaaagacca gagatcctgc tgtctcctca gcatcattcc aggcacagga  180
cgccagaaaa tggaatggtg ctgttgaatc aacaggttct                         220

SEQ ID NO: 12           moltype = RNA  length = 214
FEATURE                 Location/Qualifiers
misc_feature            1..214
                        note = Dengue virus construct
source                  1..214
                        mol_type = other RNA
                        organism = synthetic construct
SEQUENCE: 12
taaaacctgg gaggctgcga ctagcggtta gaggagaccc ctcccatgac acaacgcagc  60
agcggggccc aagactagag gttagaggag accccccgca aataaaaaca gcatattgac  120
```

-continued

```
gctgggagag accagagatc ctgctgtctc ctcagcatca ttccaggcac agaacgccag  180
aaaatggaat ggtgctgttg aatcaacagg ttct                              214

SEQ ID NO: 13           moltype = RNA  length = 219
FEATURE                 Location/Qualifiers
misc_feature            1..219
                        note = Dengue virus construct
source                  1..219
                        mol_type = other RNA
                        organism = synthetic construct
SEQUENCE: 13
atccccaggg aggccatgcg ccacggttag aggagacccc tcccatcact gacaaaacgc  60
agcaaaaggg ggcccaagac tagaggttag aggagacccc cccaacacaa aaacagcata  120
ttgacgctgg gaaagaccag agatcctgct gtctctgcaa catcaatcca ggcacagagc  180
gccgcaagat ggattggtgt tgttgatcca acaggttct                         219

SEQ ID NO: 14           moltype = RNA  length = 194
FEATURE                 Location/Qualifiers
misc_feature            1..194
                        note = Dengue virus construct
source                  1..194
                        mol_type = other RNA
                        organism = synthetic construct
SEQUENCE: 14
taaaaacccg ggaggctgca aaccatggaa gctgtacgca tggggtagca gactagaggt  60
tagaggagac cccccgcaca acaacaaaca gcatattgac gctgggagag accagagatc  120
ctgctgtctc tacagcatca ttccaggcac agaacgccag aaaatggaat ggtgctgttg  180
aatcaacagg ttct                                                    194

SEQ ID NO: 15           moltype = RNA  length = 196
FEATURE                 Location/Qualifiers
misc_feature            1..196
                        note = Dengue virus construct
source                  1..196
                        mol_type = other RNA
                        organism = synthetic construct
SEQUENCE: 15
taaaaaatcc gggaggccac aaaccatgga agctgtacgc atggcgtagt ggagactaga  60
ggttagagga gaccccccca aaacaaaaaa cagcatattg acgctgggaa agaccagaga  120
tcctgctgtc tcctcagcat cattccaggc acaggacgcc agaaaatgga atggtgctgt  180
tgaatcaaca ggttct                                                  196

SEQ ID NO: 16           moltype = RNA  length = 190
FEATURE                 Location/Qualifiers
misc_feature            1..190
                        note = Dengue virus construct
source                  1..190
                        mol_type = other RNA
                        organism = synthetic construct
SEQUENCE: 16
taaaacctgg gaggctgcaa actgtggaag ctgtacgcac ggtgtagcga ctagaggtta  60
gaggagaccc cccgcaaata aaaacagcat attgacgctg ggagagacca gagatcctgc  120
tgtctcctca gcatcattcc aggcacagaa cgccagaaaa tggaatggtg ctgttgaatc  180
aacaggttct                                                         190

SEQ ID NO: 17           moltype = RNA  length = 195
FEATURE                 Location/Qualifiers
misc_feature            1..195
                        note = Dengue virus construct
source                  1..195
                        mol_type = other RNA
                        organism = synthetic construct
SEQUENCE: 17
atccccaggg aggccatgcg ccacggaagc tgtacgcgtg gcatattgga ctagactaga  60
ggttagagga gaccccccca acacaaaaac agcatattga cgctgggaaa gaccagagat  120
cctgctgtct ctgcaacatc aatccaggca cagagcgccg caagatggat tggtgttgtt  180
gatccaacag gttct                                                   195

SEQ ID NO: 18           moltype = DNA  length = 39
FEATURE                 Location/Qualifiers
misc_feature            1..39
                        note = Junction region
source                  1..39
                        mol_type = other DNA
                        organism = synthetic construct
SEQUENCE: 18
gagggagcca tttggtaaac gtaggaagtg aaaaagagg                         39
```

```
SEQ ID NO: 19            moltype = AA   length = 5
FEATURE                  Location/Qualifiers
REGION                   1..5
                         note = Junction region
source                   1..5
                         mol_type = protein
                         organism = synthetic construct
SEQUENCE: 19
EGAIW                                                                    5

SEQ ID NO: 20            moltype = DNA  length = 39
FEATURE                  Location/Qualifiers
misc_feature             1..39
                         note = Junction region
source                   1..39
                         mol_type = other DNA
                         organism = synthetic construct
SEQUENCE: 20
agtgaaggag ttctgtaatt accaacaaca aacaccaaa                              39

SEQ ID NO: 21            moltype = AA   length = 5
FEATURE                  Location/Qualifiers
REGION                   1..5
                         note = Junction region
source                   1..5
                         mol_type = protein
                         organism = synthetic construct
SEQUENCE: 21
SEGVL                                                                    5

SEQ ID NO: 22            moltype = DNA  length = 39
FEATURE                  Location/Qualifiers
misc_feature             1..39
                         note = Junction region
source                   1..39
                         mol_type = other DNA
                         organism = synthetic construct
SEQUENCE: 22
gagggagcca tttggtagtt aacaacaaca aacaccaaa                              39

SEQ ID NO: 23            moltype = AA   length = 5
FEATURE                  Location/Qualifiers
REGION                   1..5
                         note = Junction region
source                   1..5
                         mol_type = protein
                         organism = synthetic construct
SEQUENCE: 23
EGAIW                                                                    5

SEQ ID NO: 24            moltype = DNA  length = 26
FEATURE                  Location/Qualifiers
misc_feature             1..26
                         note = synthetic primer
source                   1..26
                         mol_type = other DNA
                         organism = synthetic construct
SEQUENCE: 24
taaaaacagc atattgacgc tgggag                                            26

SEQ ID NO: 25            moltype = DNA  length = 20
FEATURE                  Location/Qualifiers
misc_feature             1..20
                         note = synthetic primer
source                   1..20
                         mol_type = other DNA
                         organism = synthetic construct
SEQUENCE: 25
gactagaggt tagaggagac                                                   20

SEQ ID NO: 26            moltype = DNA  length = 23
FEATURE                  Location/Qualifiers
misc_feature             1..23
                         note = Synthetic primer
source                   1..23
                         mol_type = other DNA
                         organism = synthetic construct
```

```
SEQUENCE: 26
gactagcggt tagaggagac ccc                                                23

SEQ ID NO: 27           moltype = DNA   length = 21
FEATURE                 Location/Qualifiers
misc_feature            1..21
                        note = synthetic primer
source                  1..21
                        mol_type = other DNA
                        organism = synthetic construct
SEQUENCE: 27
tcgggccccg ctgctgcgtt g                                                  21

SEQ ID NO: 28           moltype = DNA   length = 21
FEATURE                 Location/Qualifiers
misc_feature            1..21
                        note = synthetic primer
source                  1..21
                        mol_type = other DNA
                        organism = synthetic construct
SEQUENCE: 28
ttgggccccg ctgctgcgtt g                                                  21

SEQ ID NO: 29           moltype = DNA   length = 20
FEATURE                 Location/Qualifiers
misc_feature            1..20
                        note = synthetic primer
source                  1..20
                        mol_type = other DNA
                        organism = synthetic construct
SEQUENCE: 29
tgtgtcatgg gagggtctc                                                     20

SEQ ID NO: 30           moltype = DNA   length = 23
FEATURE                 Location/Qualifiers
misc_feature            1..23
                        note = syntetic primer
source                  1..23
                        mol_type = other DNA
                        organism = synthetic construct
SEQUENCE: 30
gctacaccgt gcgtacagct tcc                                                23

SEQ ID NO: 31           moltype = DNA   length = 23
FEATURE                 Location/Qualifiers
misc_feature            1..23
                        note = synthetic primer
source                  1..23
                        mol_type = other DNA
                        organism = synthetic construct
SEQUENCE: 31
gcagcctccc aggttttacg tcc                                                23

SEQ ID NO: 32           moltype = DNA   length = 27
FEATURE                 Location/Qualifiers
misc_feature            1..27
                        note = synthetic primer
source                  1..27
                        mol_type = other DNA
                        organism = synthetic construct
SEQUENCE: 32
aacaacaaca aacaccaaag gctattg                                            27

SEQ ID NO: 33           moltype = DNA   length = 23
FEATURE                 Location/Qualifiers
misc_feature            1..23
                        note = synthetic primer
source                  1..23
                        mol_type = other DNA
                        organism = synthetic construct
SEQUENCE: 33
cctaccggta ccagaacctg ttg                                                23
```

DEVELOPMENT OF DENGUE VIRUS VACCINE COMPONENTS

CROSS REFERENCE TO RELATED APPLICATIONS

This application is a continuation of U.S. patent application Ser. No. 17/724,037, filed Apr. 19, 2022, which is a continuation of U.S. patent application Ser. No. 16/912,359, filed Jun. 25, 2020, which is a continuation of U.S. patent application Ser. No. 16/173,217, filed Oct. 29, 2018, which is a continuation of U.S. patent application Ser. No. 14/742,533, filed Jun. 17, 2015, which is a continuation of U.S. patent application Ser. No. 13/692,557, filed Dec. 3, 2012, which is a divisional application of U.S. patent application Ser. No. 12/376,756, filed Dec. 17, 2009, which is a National Phase of International Application No. PCT/US2007/076004, filed on Aug. 15, 2007, which claims the benefit of U.S. Provisional Application No. 60/837,723, filed Aug. 15, 2006. The disclosures of each of these applications are hereby expressly incorporated by reference in their entirety.

FIELD OF THE INVENTION

The invention relates to mutations in the 3' untranslated region of the genome of dengue virus serotypes 1, 2, 3, and 4 that are useful in attenuating the growth characteristics of dengue virus vaccines.

DESCRIPTION OF THE RELATED ART

There are four serotypes of dengue virus (dengue virus type 1 [DEN1], DEN2, DEN3, and DEN4) that annually cause an estimated 50 to 100 million cases of dengue fever and 500,000 cases of the more severe form of dengue virus infection known as dengue hemorrhagic fever/dengue shock syndrome (Gubler, D. J. and M. Meltzer 1999 *Adv Virus Res* 53:35-70). Dengue virus is widely distributed throughout the tropical and semitropical regions of the world, and the number of dengue virus infections continues to increase due to the expanding range of its *Aedes aegypti* mosquito vector. A vaccine is not available for the control of dengue disease despite its importance as a reemerging disease. The goal of immunization is to protect against dengue virus disease by the induction of a long-lived neutralizing antibody response against each of the four serotypes. Simultaneous protection against all four serotypes is required, since an increase in disease severity can occur in persons with preexisting antibodies to a heterotypic dengue virus. Such immunization can be achieved economically with a live, attenuated virus vaccine.

Dengue viruses are positive-sense RNA viruses belonging to the Flavivirus genus. The approximately 1 1,000-base genome contains a single open reading frame encoding a polyprotein which is processed by proteases of both viral and cellular origin into three structural proteins (C, prM, and E) and at least seven nonstructural (NS) proteins. Both ends of the dengue virus genome contain an untranslated region (UTR), and the overall genome organization is 5MJTR-C-prM-E-NSI-NS2A-NS2B-NS3-NS4A-NS4B-NS5-UTR-3'. The 3' UTR is nearly 400 bases in length and is predicted to contain several stem-loop structures conserved among dengue virus serotypes (Brinton, M. A. et al. 1986 *Virology* 153:113-121, Hahn, C. S. et al. 1987 *J Mol Biol* 198:33-41, Proutski, V. et al. 1997 *Nucleic Acids Res* 25:1194-1202, Rauscher, S. et al. 1997 *RNA* 3:779-791, Shurtleff, A. et al. 2001 *Virology* 281:75-87). One such stem-loop structure, identified as TL-2 in the proposed secondary structure of the 3' UTR (Proutski, V. et al. 1997 *Nucleic Acids Res* 25:1194-1202), was previously removed by deletion of 30 nucleotides from the DEN4 genome (3' nucleotides 172 to 143) (Men, R. et al. 1996 *J Viral* 70:3930-3937) and has subsequently been designated as the Δ30 mutation (Durbin, A. P. et al. 2001 *Am J Trap Med Hyg* 65:405-413). The resulting virus, rDEN4Δ30, was shown to be attenuated in rhesus monkeys compared to parental viruses containing an intact TL-2 sequence and is attenuated in humans (Durbin, A. P. et al. 2001 *Am J Trap Med Hyg* 65:405-413).

SUMMARY OF THE INVENTION

The invention is related to a dengue virus or chimeric dengue virus comprising a mutation in the 3' untranslated region (3'-UTR) selected from the group consisting of:
a Δ30 mutation that removes the TL-2 homologous structure in each of the dengue virus serotypes 1, 2, 3, and 4, and nucleotides additional to the Δ30 mutation deleted from the 3'-UTR that removes sequence in the 5' direction as far as the 5' boundary of the TL-3 homologous structure in each of the dengue virus serotypes 1, 2, 3, and 4; and
(b) a replacement of the 3'-UTR of a dengue virus of a first serotype with the 3 '-UTR of a dengue virus of a second serotype, optionally containing the 430 mutation and nucleotides additional to the 430 mutation deleted from the 3'-UTR;
and immunogenic compositions, methods of inducing an immune response, and methods of producing a dengue virus or chimeric dengue virus.

BRIEF DESCRIPTION OF THE DRAWINGS

FIG. 1. Two approaches to attenuate dengue viruses. A) (a-c) Deletion of additional nucleotides from the 3'-UTR (DEN3 wt Sleman/78, SEQ ID NO: 1). B) Replacement of the 3'-UTR of a dengue virus of a first serotype with the 3'-UTR of a dengue virus of a second serotype.

FIG. 13. Δ30/31 deletion mutation depicted for each of the dengue virus serotypes DEN1, DEN2, DEN3 and DEN4. In addition to the deletion of the nucleotides comprising the Δ30 mutation, the Δ31 mutation deletes nt 258 to 228 of DEN1, DEN2, DEN3, and DEN4, with reverse-direction numbering system. The deleted region is indicated by the Δ symbol. The nucleotide sequence shown in FIG. 3:—SEQ ID NO: 13.

DETAILED DESCRIPTION OF THE PREFERRED EMBODIMENT

Definitions

Figure 1A:
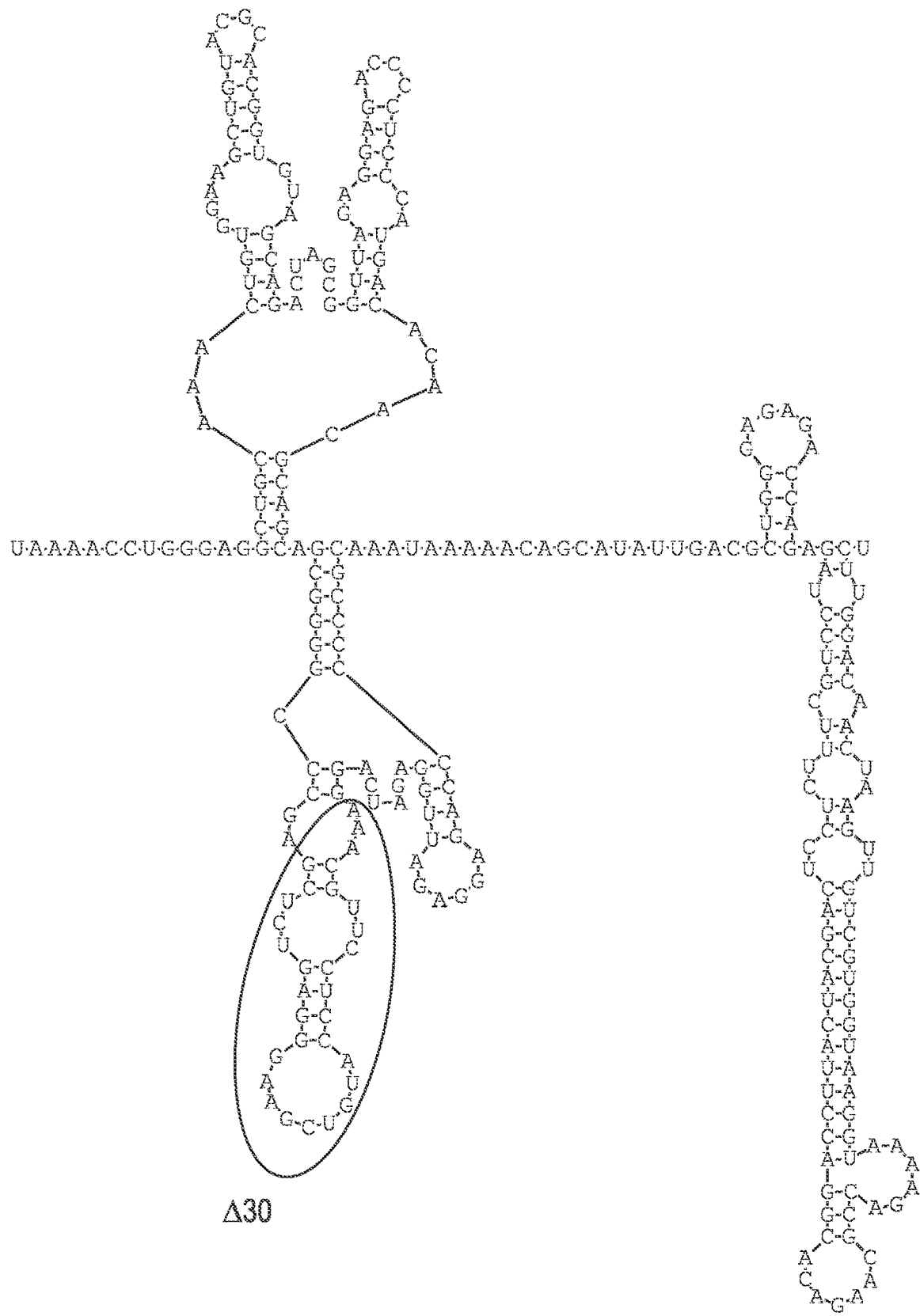
FIG. 1a is a magnified version of FIG. 1 in the portion designated as A(a).

Unless defined otherwise, technical and scientific terms used herein have the same meaning as commonly understood by one of ordinary skill in the art to which this invention belongs. See, e.g., Singleton P and Sainsbury D., Dictionary of Microbiology and Molecular Biology 3rd ed., J. Wiley & Sons, Chichester, New York, 2001, and Fields Virology 4th ed., Knipe D.M. and Howley P.M. eds, Lippincott Williams & Wilkins, Philadelphia 2001.

The term "about" means within 1,2, or 3 nucleotides.

Mutant Dengue Viruses and Chimeric Dengue Viruses

A goal of the invention is to develop a set of type-specific, live attenuated dengue vaccine components that can be formulated into a safe, effective, and economical tetravalent dengue vaccine. The Δ30 mutation attenuates DEN4 in rhesus monkeys (Men. R. et al. 1996 *J Viral* 70:3930-3937)). The Δ30 mutation removes a homologous structure (TL-2) in each of the dengue virus serotypes 1, 2, 3, and 4 (FIGS. 2-5). However, the Δ30 mutation was found to not attenuate DEN 3 in rhesus monkeys.

An embodiment of the invention provides dengue viruses and chimeric dengue viruses having one or more mutations that result in attenuation, methods of making such dengue viruses, and methods for using these dengue viruses to prevent or treat dengue virus infection. The mutation (or mutations) in the dengue virus of the invention is present in the 3' untranslated region (3'-UTR) formed by the most downstream approximately 384 nucleotides of the viral RNA, which have been shown to play a role in determining attenuation. The viruses and methods of the invention are described further, as follows.

One example of a dengue virus that can be used in the invention is the serotype 3, Sleman/78 strain. The applicability of the invention to all members of the dengue virus taxonomic group is inferred by the observation that the properties of other dengue virus strains are similar to that of any one dengue virus strain. Dengue viruses have been grouped into four serotypes (DEN1. DEN2, DENS and DEN4). Numerous strains have been identified for each of the four serotypes. The complete genomic sequences of various dengue virus strains are provided as Genbank accession numbers in Table A.

TABLE A

Examples of Dengue Virus Strains

| Serotype | Strain | Accession No. |
|---|---|---|
| 1 | 02-20 | AB178040 |
| 1 | 16007 | AF180817 |
| 1 | 16007 PDK-13 | AF180818 |

TABLE A-continued

Examples of Dengue Virus Strains

| Serotype | Strain | Accession No. |
|---|---|---|
| 1 | 259par00 | AF514883 |
| 1 | 280par00 | AF514878 |
| 1 | 293arg00 | AY206457 |
| 1 | 295arg00 | AF514885 |
| 1 | 297arg00 | AF514889 |
| 1 | 301arg00 | AF514876 |
| 1 | 98901518 | AB189120 |
| 1 | 98901530 | AB189121 |
| 1 | A88 | AB074761 |
| 1 | Abidjan | AF298807 |
| 1 | ARG0028 | AY277665 |
| 1 | ARG0048 | AY277666 |
| 1 | ARG9920 | AY277664 |
| 1 | BR-90 | AF226685 |
| 1 | BR-01-MR | AF513110 |
| 1 | BR-97-111 | AF311956 |
| 1 | BR-97-233 | AF311958 |
| 1 | BR-97-409 | AF311957 |
| 1 | Cambodia | AF309641 |
| 1 | FGA-89 | AF226687 |
| 1 | FGA-NA d1d | AF226686 |
| 1 | Fj231-04 | DQ193572 |
| 1 | GD05-99 | AY376738 |
| 1 | GD23-95 | AY373427 |
| 1 | GZ-80 | AF350498 |
| 1 | D1-hu-Yap-NIID27-2004 | AB204803 |
| 1 | D1-H-IMTSSA-98-606 | AF298808 |
| 1 | Mochizuki | AB074760 |
| 1 | D1.Myanmar.059-01 | AY708047 |
| 1 | D1.Myanmar.194-01 | AY713474 |
| 1 | D1.Myanmar.206-01 | AY713475 |
| 1 | D1.Myanmar.23819-96 | AY722802 |
| 1 | D1.Myanmar.305-01 | AY713476 |
| 1 | D1.Myanmar.31459-98 | AY726555 |
| 1 | D1.Myanmar.31987-98 | AY726554 |
| 1 | D1.Myanmar.32514-98 | AY722803 |
| 1 | D1.Myanmar.37726-01 | AY726549 |
| 1 | D1.Myanmar.38862-01 | AY726550 |
| 1 | D1.Myanmar.40553-71 | AY713473 |
| 1 | D1.Myanmar.40568-76 | AY722801 |
| 1 | D1.Myanmar.44168-01 | AY726551 |
| 1 | D1.Myanmar.44988-02 | AY726552 |
| 1 | D1.Myanmar.49440-02 | AY726553 |
| 1 | rWestern Pacific-delta30 | AY145123 |
| 1 | Western Pacific rDEN1mutF | AY145122 |
| 1 | S275-90 | A75711 |
| 1 | D1-hu-Seychelles-NIID41-2003 | AB195673 |
| 1 | Singapore 8114-93 | AY762084 |
| 1 | Singapore S275-90 | M87512 |
| 1 | ThD1_0008_81 | AY732483 |
| 1 | ThD1_0049_01 | AY732482 |
| 1 | ThD1_0081_82 | AY732481 |
| 1 | ThD1_0097_94 | AY732480 |
| 1 | ThD1_0102_01 | AY732479 |
| 1 | ThD1_0323_91 | AY732478 |
| 1 | ThD1_0336_91 | AY732477 |
| 1 | ThD1_0442_80 | AY732476 |
| 1 | ThD1_0488_94 | AY732475 |
| 1 | ThD1_0673_80 | AY732474 |
| 1 | Recombinant Western Pacific | AY145121 |
| 1 | Nauru Island Western Pacific 45AZ5 | NC_001477 |
| 1 | Nauru Island, Western Pacific Bethesda | U88535 |
| 1 | Nauru Island Western Pacific 45AZ5-PDK27 | U88537 |
| 2 | 131 | AF100469 |
| 2 | 16681-PDK53 | M84728 |
| 2 | 16681 Blok | M84727 |
| 2 | 16681 Kinney | U87411 |
| 2 | 43 | AF204178 |
| 2 | 44 | AF204177 |
| 2 | 98900663 | AB189122 |
| 2 | 98900665 | AB189123 |
| 2 | 98900666 | AB189124 |
| 2 | BA05i | AY858035 |
| 2 | Bangkok 1974 | AJ487271 |

TABLE A-continued

Examples of Dengue Virus Strains

| Serotype | Strain | Accession No. |
|---|---|---|
| 2 | BR64022 | AF489932 |
| 2 | C0166 | AF100463 |
| 2 | C0167 | AF100464 |
| 2 | C0371 | AF100461 |
| 2 | C0390 | AF100462 |
| 2 | China 04 | AF119661 |
| 2 | Cuba115-97 | AY702036 |
| 2 | Cuba13-97 | AY702034 |
| 2 | Cuba165-97 | AY702038 |
| 2 | Cuba205-97 | AY702039 |
| 2 | Cuba58-97 | AY702035 |
| 2 | Cuba89-97 | AY702037 |
| 2 | DR23-01 | AB122020 |
| 2 | DR31-01 | AB122021 |
| 2 | DR59-01 | AB122022 |
| 2 | FJ-10 | AF276619 |
| 2 | FJ11-99 | AF359579 |
| 2 | I348600 | AY702040 |
| 2 | IQT1797 | AF100467 |
| 2 | IQT2913 | AF100468 |
| 2 | Jamaica-N.1409 | M20558 |
| 2 | K0008 | AF100459 |
| 2 | K0010 | AF100460 |
| 2 | Mara4 | AF100466 |
| 2 | DEN2-H-IMTSSA-MART-98-703 | AF208496 |
| 2 | New Guinea C | AF038403 |
| 2 | New Guinea C-PUO-218 hybrid | AF038402 |
| 2 | New Guinea-C | M29095 |
| 2 | PDK-53 | U87412 |
| 2 | S1 vaccine | NC_001474 |
| 2 | TB16i | AY858036 |
| 2 | ThD2_0017_98 | DQ181799 |
| 2 | ThD2_0026_88 | DQ181802 |
| 2 | ThD2_0038_74 | DQ181806 |
| 2 | ThD2_0055_99 | DQ181798 |
| 2 | ThD2_0078_01 | DQ181797 |
| 2 | ThD2_0168_79 | DQ181805 |
| 2 | ThD2_0263_95 | DQ181800 |
| 2 | ThD2_0284.90 | DQ181801 |
| 2 | ThD2_0433_85 | DQ181803 |
| 2 | ThD2_0498_84 | DQ181804 |
| 2 | ThNH-28-93 | AF022435 |
| 2 | ThNH29-93 | AF169678 |
| 2 | ThNH36-93 | AF169679 |
| 2 | ThNH45-93 | AF169680 |
| 2 | ThNH-52-93 | AF022436 |
| 2 | ThNH54-93 | AF169682 |
| 2 | ThNH55-93 | AF169681 |
| 2 | ThNH62-93 | AF169683 |
| 2 | ThNH63-93 | AF169684 |
| 2 | ThNH69-93 | AF169685 |
| 2 | ThNH73-93 | AF169686 |
| 2 | ThNH76-93 | AF169687 |
| 2 | ThNH81-93 | AF169688 |
| 2 | ThNH-p36-93 | AF022441 |
| 2 | ThNH-7-93 | AF022434 |
| 2 | ThNH-p11-93 | AF022437 |
| 2 | ThNH-p12-93 | AF022438 |
| 2 | ThNH-p14-93 | AF022439 |
| 2 | ThNH-p16-93 | AF022440 |
| 2 | Tonga-74 | AY744147 |
| 2 | TSV01 | AY037116 |
| 2 | Taiwan-1008DHF | AY776328 |
| 2 | Ven2 | AF100465 |
| 3 | D3-H-IMTSSA-MART-1999-1243 | AY099337 |
| 3 | D3-H-IMTSSA-SRI-2000-1266 | AY099336 |
| 3 | 80-2 | AF317645 |
| 3 | 98901403 | AB189125 |
| 3 | 98901437 | AB189126 |
| 3 | 98901517 | AB189127 |
| 3 | 98902890 | AB189128 |
| 3 | BA51 | AY858037 |
| 3 | BDH02-1 | AY496871 |
| 3 | BDH02-3 | AY496873 |
| 3 | BDH02-4 | AY496874 |
| 3 | BDH02-7 | AY496877 |
| 3 | BR74886-02 | AY679147 |
| 3 | C0331-94 | AY876494 |
| 3 | C0360-94 | AY923865 |
| 3 | den3_88 | AY858038 |
| 3 | den3_98 | AY858039 |
| 3 | FW01 | AY858040 |
| 3 | FW06 | AY858041 |
| 3 | H87 | NC_001475 |
| 3 | D3-Hu-TL018NIID-2005 | AB214879 |
| 3 | D3-Hu-TL029NIID-2005 | AB214880 |
| 3 | D3-Hu-TL109NIID-2005 | AB214881 |
| 3 | D3-Hu-TL129NIID-2005 | AB214882 |
| 3 | InJ_16_82 | DQ401690 |
| 3 | KJ30i | AY858042 |
| 3 | KJ46 | AY858043 |
| 3 | KJ71 | AY858044 |
| 3 | mutant BDH02_01 | DQ401689 |
| 3 | mutant BDH02_03 | DQ401691 |
| 3 | mutant BDH02_04 | DQ401692 |
| 3 | mutant BDH02_07 | DQ401693 |
| 3 | mutant InJ_I6_82 | DQ401694 |
| 3 | mutant PhMH_J1_97 | DQ401695 |
| 3 | PF89-27643 | AY744677 |
| 3 | PF89-320219 | AY744678 |
| 3 | PF90-3050 | AY744679 |
| 3 | PF90-3056 | AY744680 |
| 3 | PF90-6056 | AY744681 |
| 3 | PF92-2956 | AY744682 |
| 3 | PF92-2986 | AY744683 |
| 3 | PH86 | AY858045 |
| 3 | PhMH-J1-97 | AY496879 |
| 3 | PI64 | AY858046 |
| 3 | Singapore | AY662691 |
| 3 | Singapore 8120-95 | AY766104 |
| 3 | Sleman-78 | AY648961 |
| 3 | TB16 | AY858047 |
| 3 | TB55i | AY858048 |
| 3 | ThD3 0007 87 | AY676353 |
| 3 | ThD3 0010 87 | AY676353 |
| 3 | ThD3 0055 93 | AY676351 |
| 3 | ThD3 0104 93 | AY676350 |
| 3 | ThD3 1283 98 | AY676349 |
| 3 | ThD3 1687 98 | AY676348 |
| 3 | PF92-4190 | AY744684 |
| 3 | PF94-136116 | AY744685 |
| 3 | Taiwan-739079A | AY776329 |
| 4 | 2A | AF375822 |
| 4 | Recombinant clone rDEN4 | AF326825 |
| 4 | 2Adel30 | AF326826 |
| 4 | 814669 | AF326573 |
| 4 | B5 | AF289029 |
| 4 | rDEN4del30 | AF326827 |
| 4 | H241 | AY947539 |
| 4 | rDEN4 | NC_002640 |
| 4 | Singapore 8976-95 | AY762085 |
| 4 | SW38i | AY858050 |
| 4 | ThD4_0017_97 | AY618989 |
| 4 | ThD4_0087_77 | AY618991 |
| 4 | ThD4_0348_91 | AY618990 |
| 1 | ThD4_0476_97 | AY618988 |
| 4 | ThD4_0485_01 | AY618992 |
| 4 | ThD4_0734_00 | AY618993 |
| 4 | Taiwan-2K0713 | AY776330 |
| 4 | Unknown | M14931 |

Mutations can be made in the 3'-UTR of a wild type infectious clone, e.g., dengue virus serotype 3, strain Slemarif78 or an infectious clone of another wild type, virulent dengue virus, and the mutants can then be tested in an animal model system (e.g., in mouse and/or monkey model systems) to identify sites that cause attenuation. Attenuation is judged by, for example, detection of decreased vireinia. One or more additional mutations found to attenuate the wild-type virus are optionally introduced into a wild type dengue virus, and these mutants are tested in an animal model system (e.g., in a mouse and/or a monkey model system) to determine whether the resulting mutants are attenuated. Mutants that are found to be attenuated can then be used as new vaccine strains that have increased safety, due to attenuation.

In addition to the viruses listed above, dengue viruses including chimeric dengue viruses that include one or more attenuating mutations are included in the invention. These chimeras can consist of a dengue virus of a first serotype (i.e., a background dengue virus) in which a structural protein (or proteins) has been replaced with a corresponding structural protein (or proteins) of a dengue virus of a second serotype. For example, the chimeras can consist of a background dengue virus in which the prM and E proteins of the dengue virus of the first serotype have been replaced with the prM and E proteins of the dengue virus of the second serotype. The chimeric viruses can be made from any combination of dengue viruses of different scrotypes. The dengues against which immunity is sought is the source of the inserted structural protein(s).

As is noted above, mutations that are included in the viruses of the present invention are attenuating. These mutations are present in the dengue virus 3'-UTR structure to attenuate the virus. Mutations can be made in the 3'-UTR using standard methods, such as site-directed mutagenesis. One example of the type of mutation present in the viruses of the invention is substitutions, hut other types of mutations, such as deletions and insertions, can be used as well. In addition, as is noted above, the mutations can be present singly or in the context of one or more additional mutations.

Figure 1B:
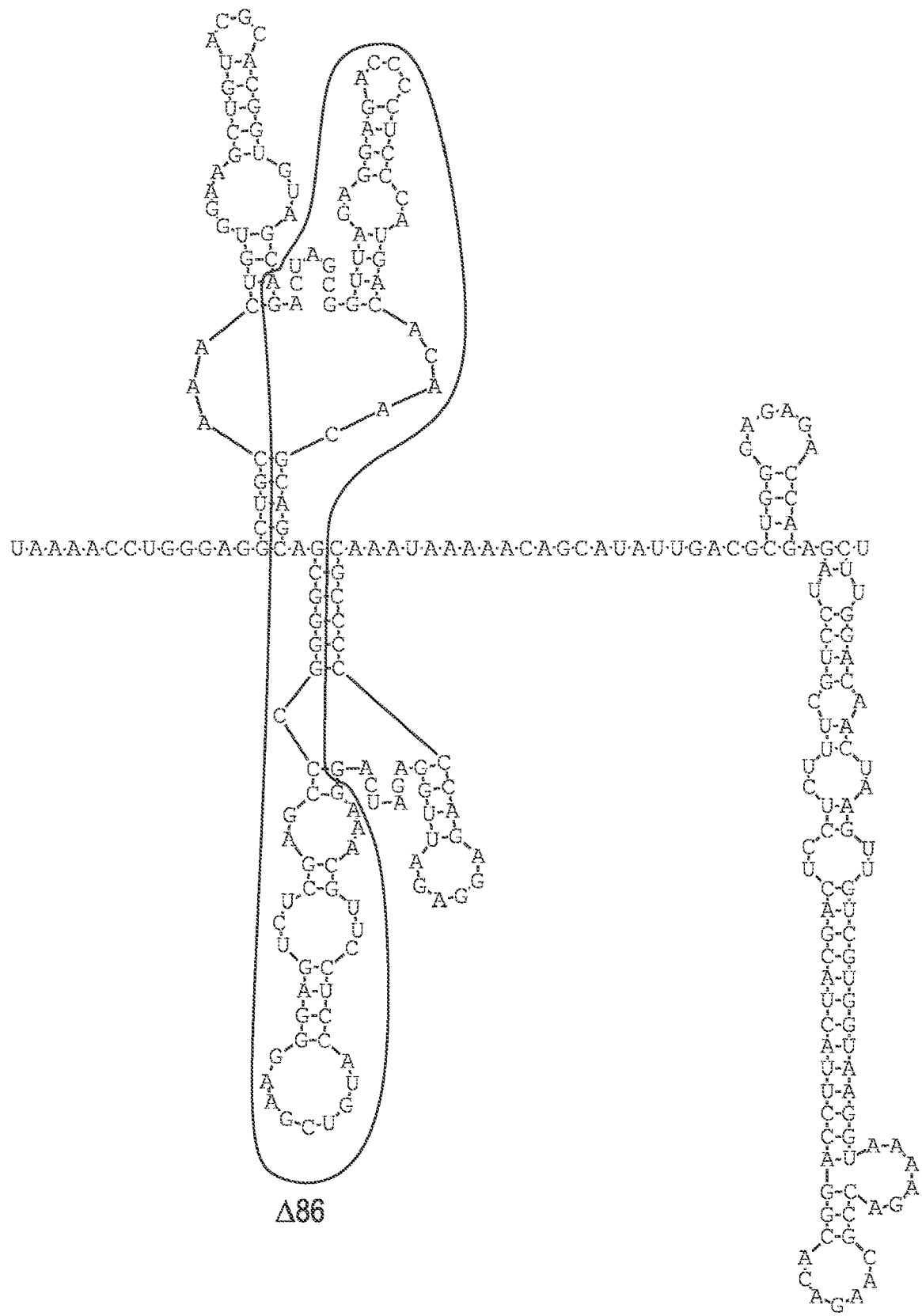
FIG. 1b is a magnified version of FIG. 1 in the portion designated as A(b).
Figure 1C:
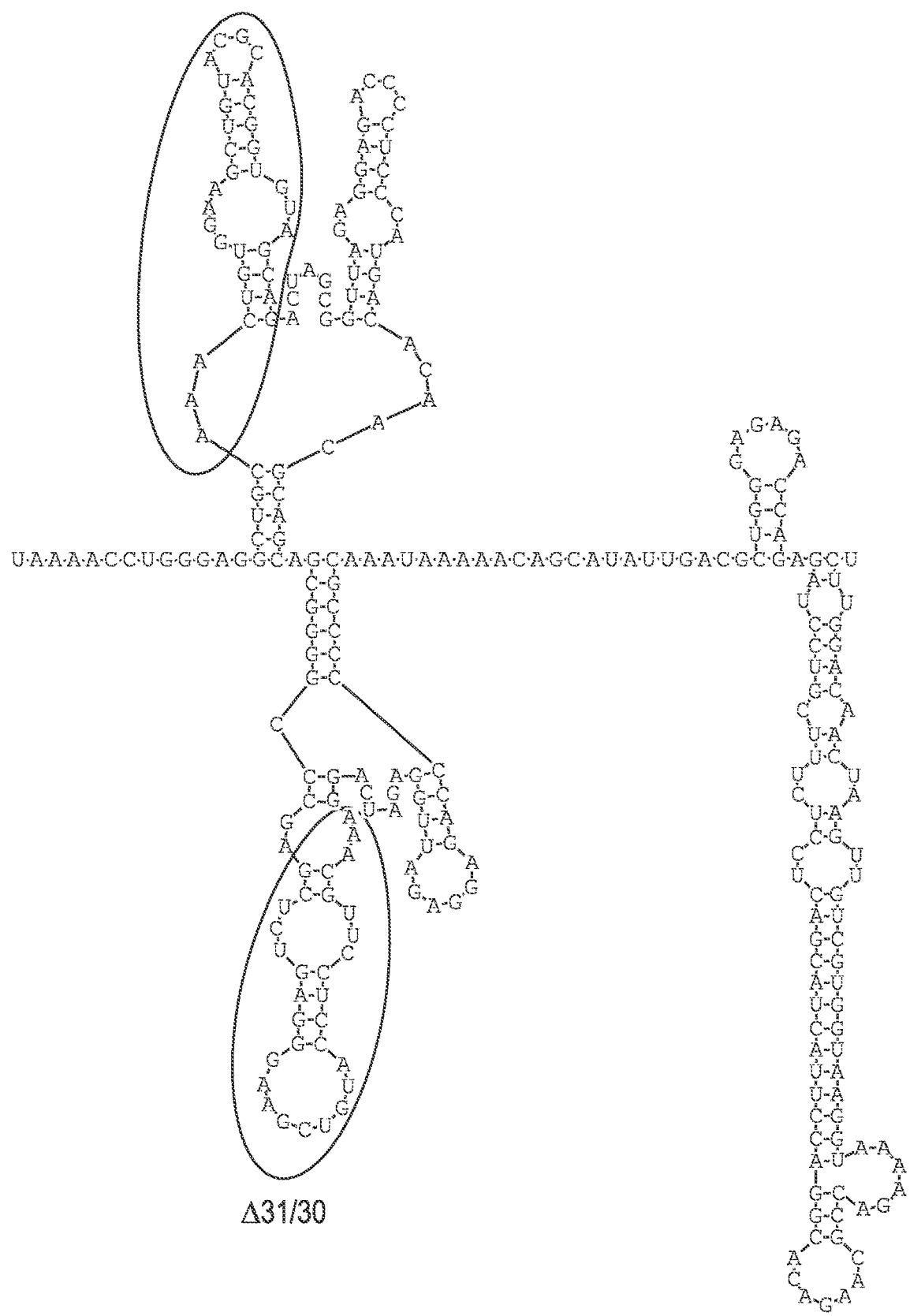
FIG. 1c is a magnified version of FIG. 1 in the portion designated as A(c).
Figure 2:
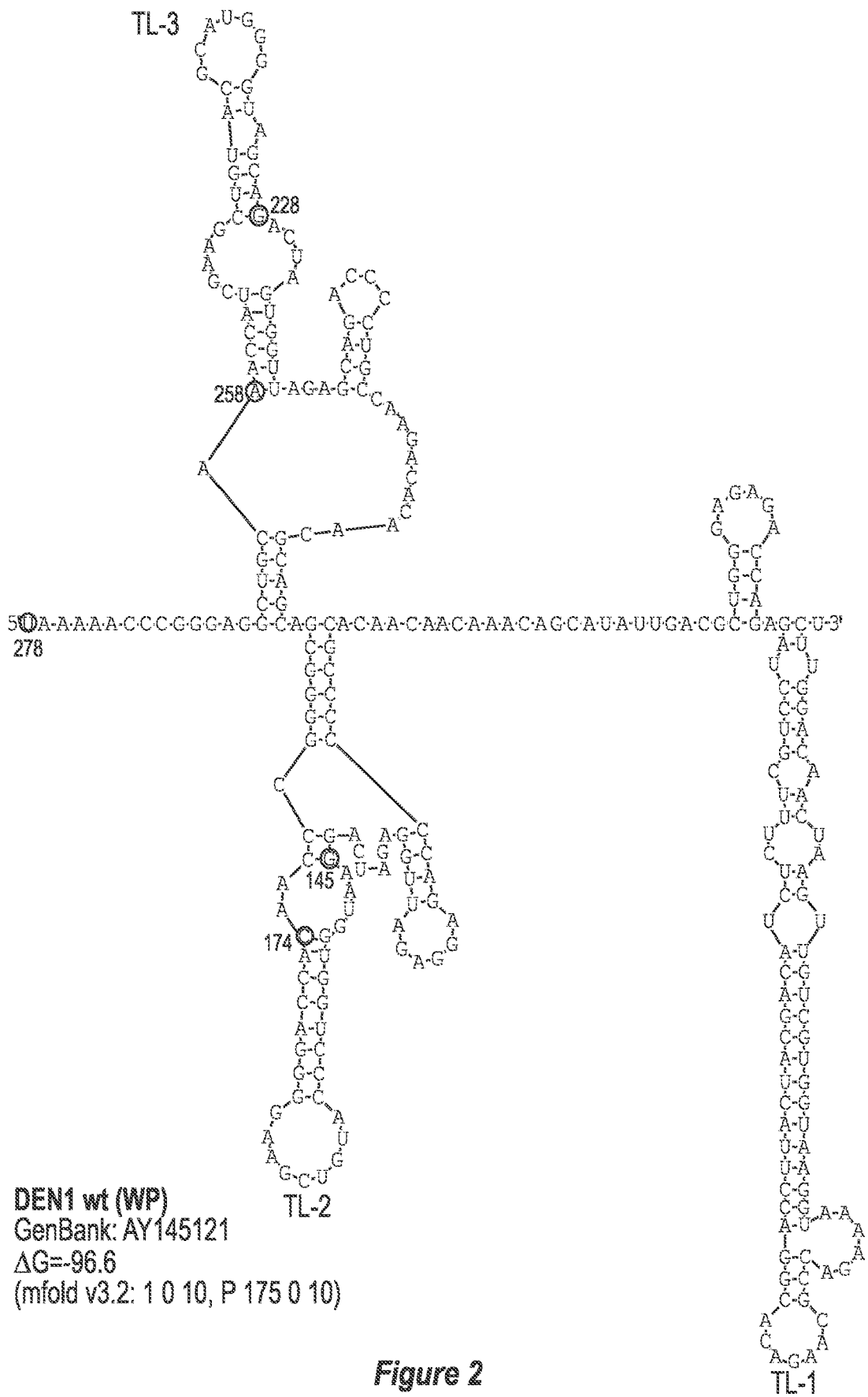
FIG. 2. Predicted secondary structure of the TL-1, TL-2 and TL-3 region of the 3'-UTR of each DEN serotype. The GenBank accession number of the sequence used for construction of each secondary structure model is indicated. Only the last 278, 281, 276 and 281 nucleotides of DEN1, DEN2, DEN3, and DEN4, respectively, which comprise TL-1, TL-2 and TL-3, are used to avoid circularization of the structure and subsequent misfolding of known and experimentally-verified structural elements. The mfold program contraints specific for each structure model are indicated. Nucleotides that border the principle deletions are circled and numbered, with nucleotide numbering beginning at the 3' genome end (reverse-direction numbering system). The nucleotide sequence shown in FIG. 2:—SEQ ID NO: 2.
Figure 3:
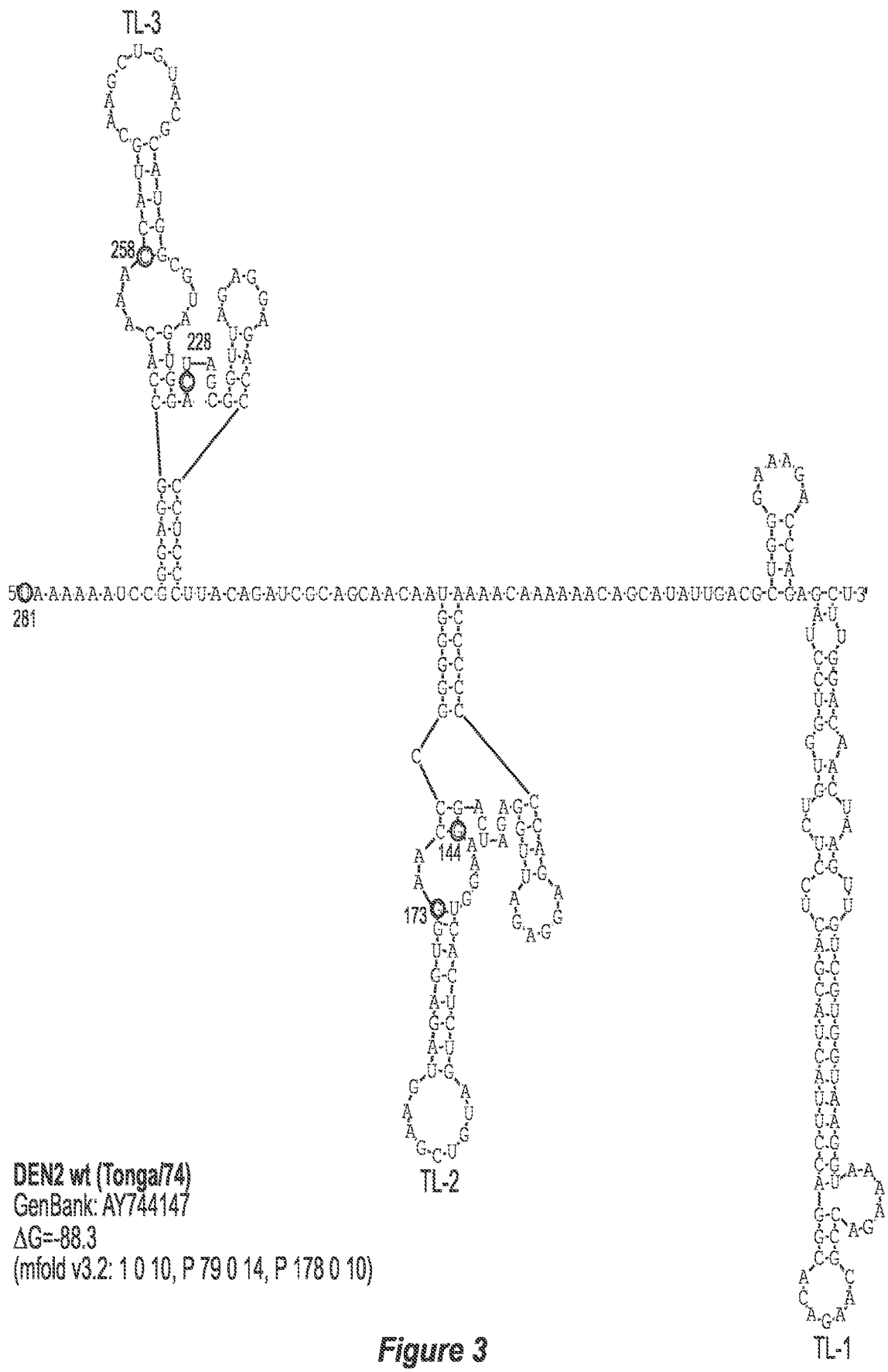
FIG. 3. Predicted secondary structure of the TL-1, TL-2 and TL-3 region of the 3'-UTR of each DEN serotype. The GenBank accession number of the sequence used for construction of each secondary structure model is indicated. Only the last 278, 281, 276 and 281 nucleotides of DEN1, DEN2, DEN3, and DEN4, respectively, which comprise TL-1, TL-2 and TL-3, are used to avoid circularization of the structure and subsequent misfolding of known and experimentally-verified structural elements. The refold program contraints specific for each structure model are indicated. Nucleotides that border the principle deletions are circled and numbered, with nucleotide numbering beginning at the 3' genome end (reverse-direction numbering system). The nucleotide sequence shown in FIG. 3:—SEQ ID NO: 3.

Referring to FIG. 1, two approaches were taken to attenuate dengue virus. In one aspect, nucleotides additional to the Δ30 mutation were deleted from the 3'-UTR. In another aspect, the 3'-VTR of a dengue virus of a first serotype was replaced with the 3'-UTR from a dengue virus of a second serotype (optionally containing the Δ30 mutation and nucleotides additional to the Δ30 mutation deleted from the 3'-UTR).

Deletion of Nucleotides Additional to the Δ30 Mutation from the 3'-UTR

Figure 4:
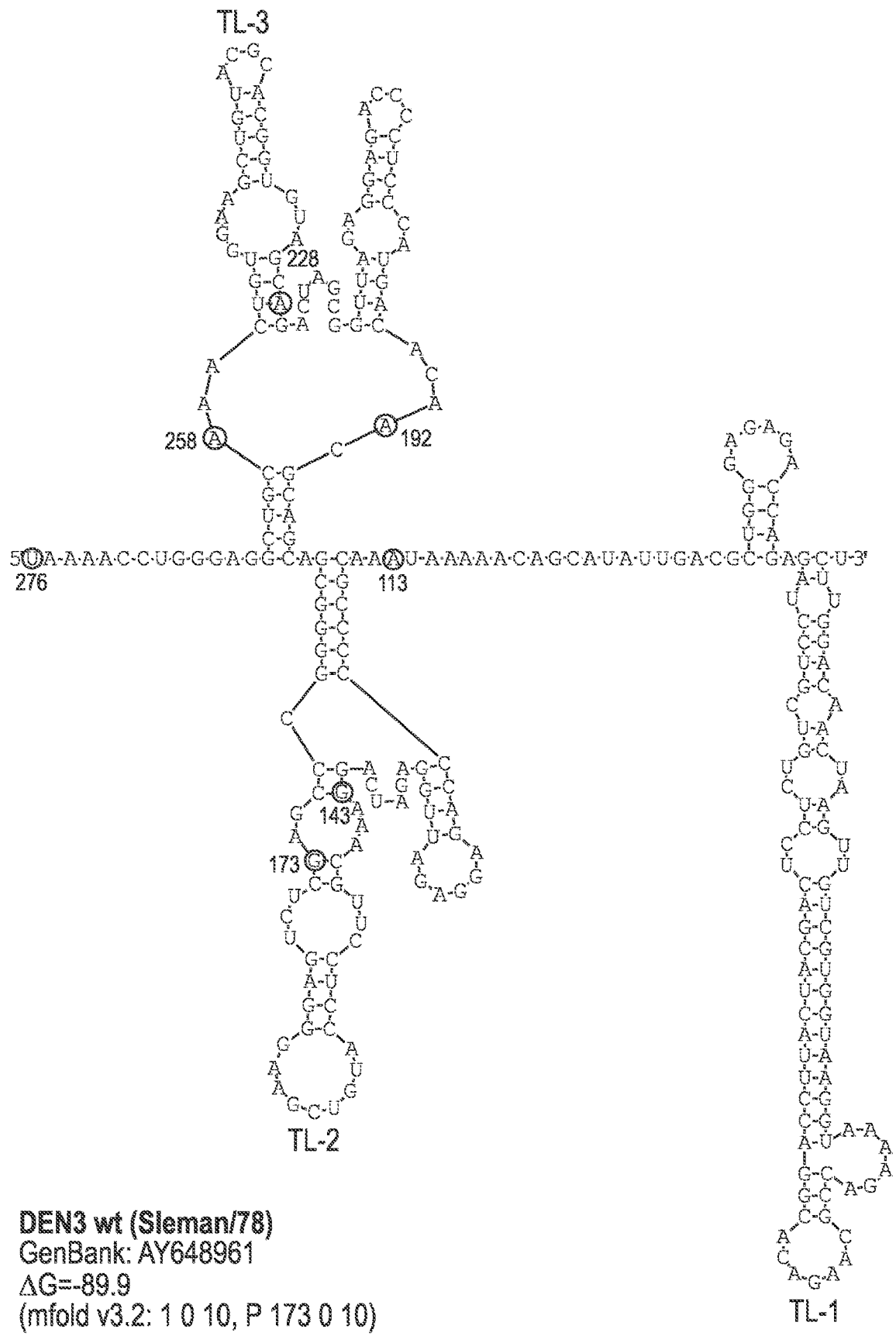
FIG. 4. Predicted secondary structure of the TL-1, TL-2 and TL-3 region of the 3'-UTR of each DEN serotype. The GenBank accession number of the sequence used for construction of each secondary structure model is indicated. Only the last 278, 281, 276 and 281 nucleotides of DEN1, DEN2, DEN3, and DEN4, respectively, which comprise TL-1, TL-2 and TL-3, are used to avoid circularization of the structure and subsequent misfolding of known and experimentally-verified structural elements. The mfold program contraints specific for each structure model are indicated. Nucleotides that border the principle deletions are circled and numbered, with nucleotide numbering beginning at the 3' genome end (reverse-direction numbering system). The nucleotide sequence shown in FIG. 4:—SEQ ID NO: 4.
Figure 5:
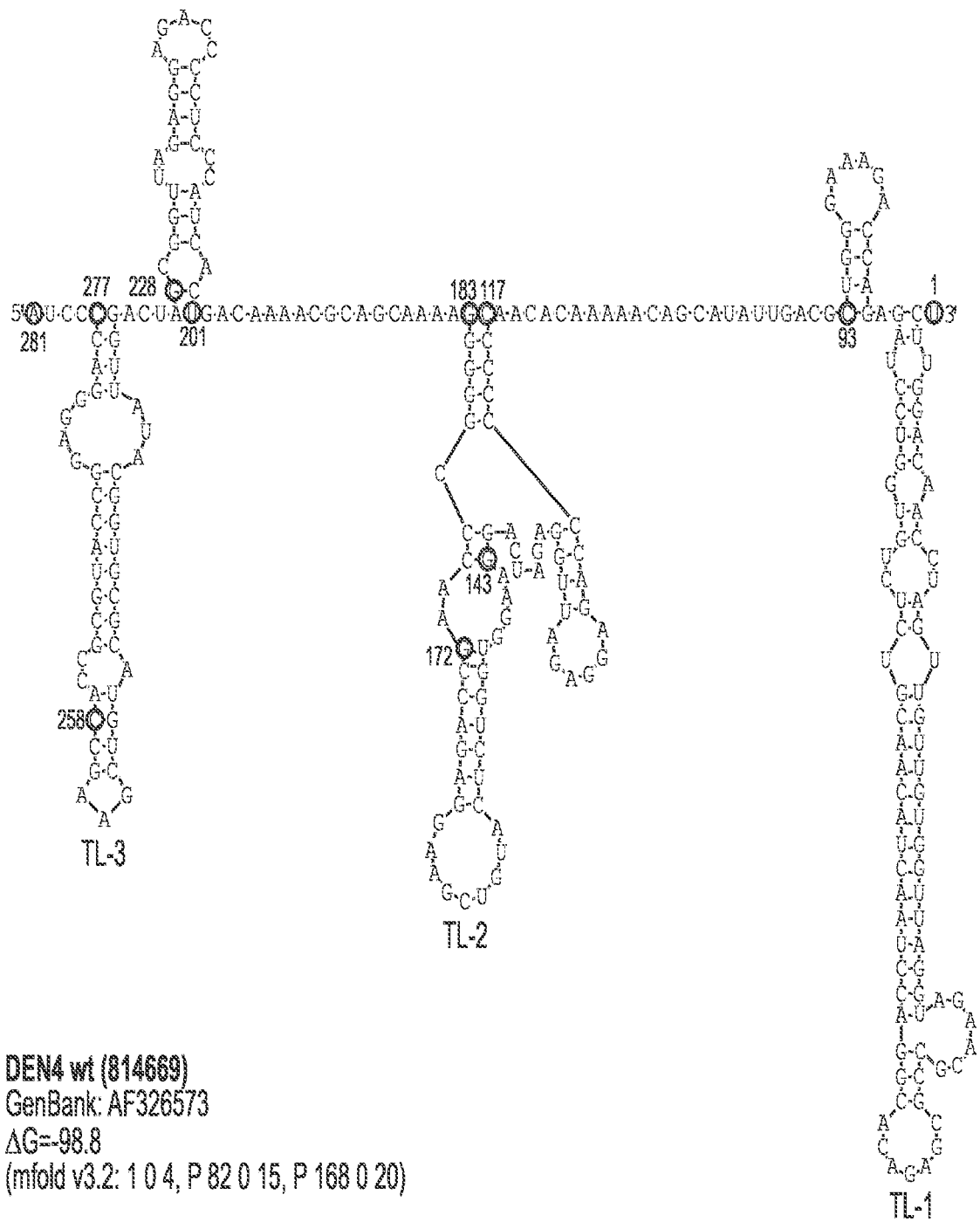
FIG. 5. Predicted secondary structure of the TL-1, TL-2 and TL-3 region of the 3'-LITR of each DEN serotype. The GenBank accession number of the sequence used for construction of each secondary structure model is indicated. Only the last 278, 281, 276 and 281 nucleotides of DEN1, DEN2, DEN3, and DEN4, respectively, which comprise n-1, TL-2 and TL-3, are used to avoid circularization of the structure and subsequent misfolding of known and experimentally-verified structural elements. The infold program contraints specific for each structure model are indicated. Nucleotides that border the principle deletions are circled and numbered, with nucleotide numbering beginning at the 3' genome end (reverse-direction numbering system). The nucleotide sequence shown in FIG. 5:—SEQ ID NO: 5.
Figure 6:
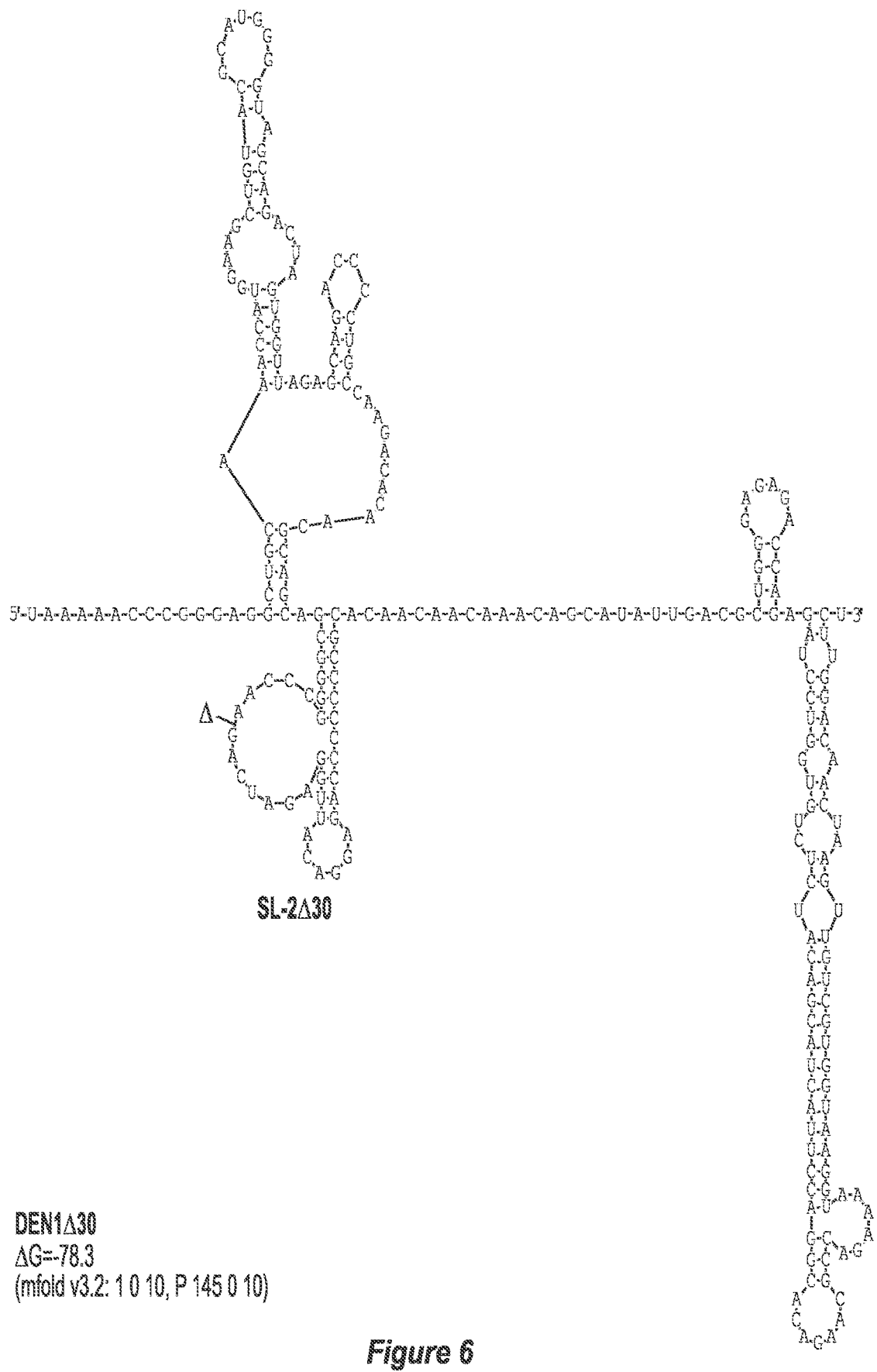
FIG. 6. Δ30 deletion mutation depicted for each of the dengue virus serotypes DEN1, DEN2, DEN3 and DEN4. The Δ30 mutation deletes nt 174 to 145 of DEN1, nt 173 to 144 of DEN2, nt 173 to 143 of DEN3, and nt 172 to 143 of DEN4, with reverse-direction numbering system. The deleted region is indicated by the Δ symbol. The nucleotide sequence shown in FIG. 6:—SEQ ID NO: 6.
Figure 7:
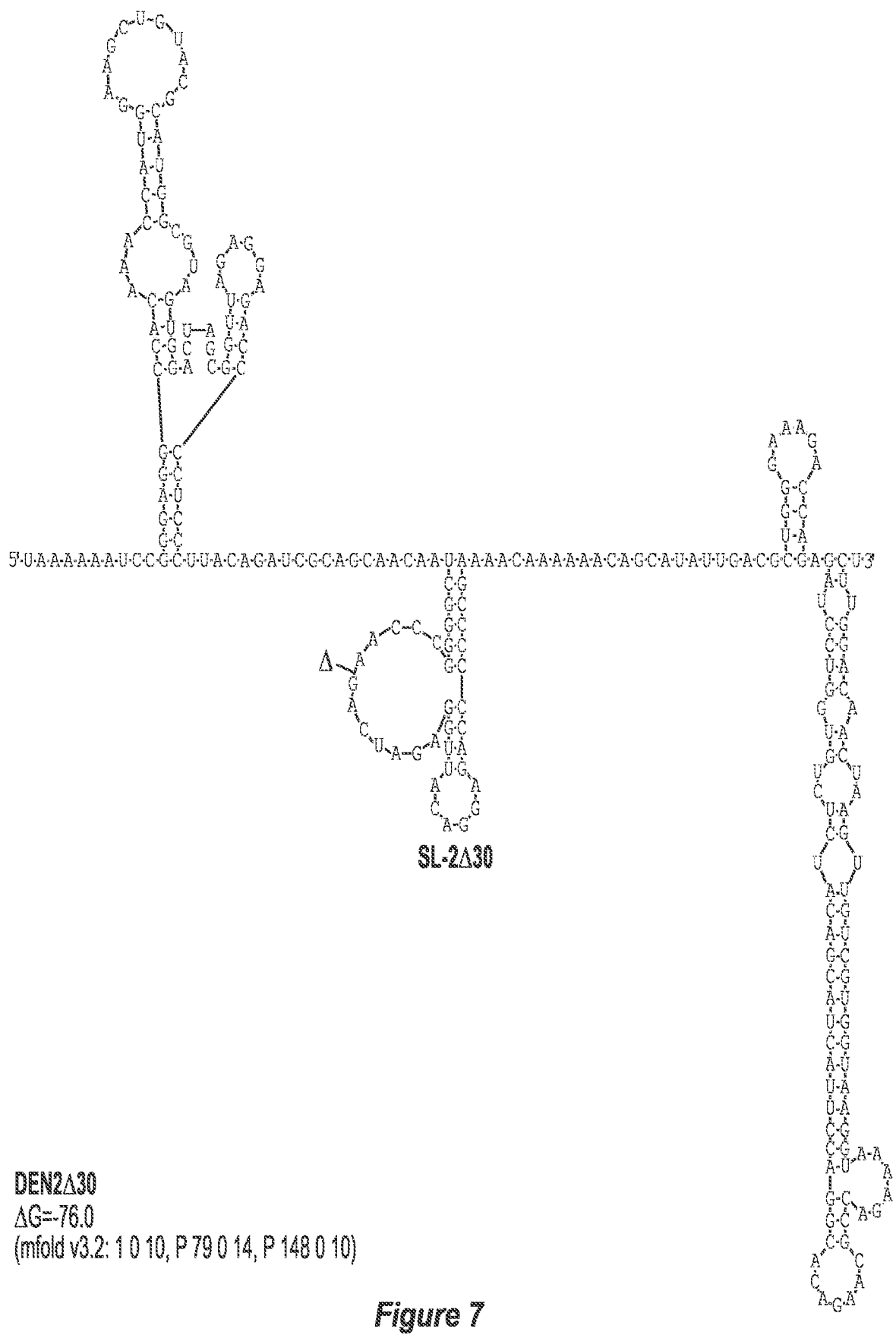
FIG. 7. Δ30 deletion mutation depicted for each of the dengue virus serotypes DEN1, DEN2, DEN3 and DEN4. The Δ30 mutation deletes nt 174 to 145 of DEN1, nt 173 to 144 of DEN2, nt 173 to 143 of DEN3, and nt 172 to 143 of DEN4, with reverse-direction numbering system. The deleted region is indicated by the Δ symbol. The nucleotide sequence shown in FIG. 7:—SEQ ID NO: 7.

Referring to FIGS. 2-5, using the first approach, the 3'-UTR of dengue viruses contain various conserved sequence motifs. The sequence of the DEN4 3'-UTR is illustrated in FIG. 5. The genome of DEN4 strain 814669 contains 10,646 nucleotides, of which the last 384 nt at the 3' terminus are untranslated (non-coding). The locations of various sequence components in this region are designated with the reverse-direction numbering system. These sequences include the 3' distal secondary structure (nt 1 to 93), predicted to form stem-loop 1 (SL-1), which contains terminal loop 1 ('IL-1). Nucleotides 117-183 form stem-loop 2 (SL-2) which contains TL-2. Nucleotides 201-277 form a pair of stem-loops (SL-3) which in part contains TL-3. Although the primary sequence of stem-loop 1 differs slightly among the dengue serotypes, the secondary structure is strictly conserved (compare FIGS. 2-5). Although the nucleotide spacing between SL-2 and neighboring SL-1 and SL-3 differ among the dengue virus serotypes, the overall structure of SL-2 is well-conserved. In addition, the exposed 9 nucleotides that comprise TL-2 are identical within all 4 dengue serotypes. It is TL-2 and its supporting stem structure that are removed by the Δ30 mutation (about nt 143-172). Removal of these 30 nucleotides results in formation of a new predicted structural element (SL-2Δ30) which has a primary sequence and secondary structure which is identical for each of the dengue virus serotypes (compare FIGS. 6-9).

FIGS. 10-13 illustrate the approach where nucleotides additional to the Δ30 mutation are deleted from the 3'-UTR. The Δ30 mutation removes the TL-2 homologous structure in each of the dengue virus serotypes 1, 2, 3, and 4. The approach where nucleotides additional to the Δ30 mutation are deleted from the 3'-.ITR removes the TL-2 homologous structure and sequence up to and optionally including the TL-3 homologous structure so that the deletion extends as far as the 5' boundary of the TL-3 homologous structure in each of the dengue virus serotypes 1, 2, 3, and 4. In the approach illustrated in FIGS. 10-14, an additional deletion of about 31 nucleotides from TL-3 results in formation of a new predicted structural element (SL-3Δ31).

Referring to FIGS. 14-17, the Δ86 mutation removes the TL-2 homologous structure and removes sequence up to the TL-3 homologous structure in each of the dengue virus serotypes DEN1, DEN2, DEN3 and DEN4. This deletion results in the formation of a new predicted structural element (SL-2Δ86).

In some embodiments that involve deletion of nucleotides additional to the Δ30) mutation, nucleic acid deletions are made to the 3'-UTR structure of the dengue virus genome to attenuate the virus while maintaining its immunogenicity. The deletions include the Δ30 deletion (nt 173-143 of the serotype 3 Slemant78 strain in an exemplary manner or corresponding thereto in other strains of DEN1, DEN2, DEN3, or DEN4; numbering is from the 3" end of the viral genome) in addition to deletion of additional 3'-UTR sequence that is contiguous or non-contiguous to the Δ30 deletion. The Δ30 deletion corresponds to the TL-2 structure of the 3'-UTR. One type of embodiment, termed rDEN1Δ30/31, rDEN2Δ30/31, rDEN3Δ30/31, or rDEN4Δ30/31 includes the original Δ30 deletion and a non-contiguous 31 nt deletion that removes both the original TL-2 and TL-3 structures. Another type of embodiment, termed rDEN I Δ61, rDEN2Δ6I, rDEN3Δ61, or rDEN4Δ61 includes the Δ30 deletion and deletion of 31 contiguous nucleotides extending 3' from the Δ30 deletion. Another type of embodiment, termed rDEN1M&, rDEN2Δ86, rDEN3Δ86, or rDEN4Δ86, includes the Δ30 deletion and deletion of 56 contiguous nucleotides extending 5' from the Δ30 deletion. For DEN3, a complete list of mutant viruses constructed to contain 3'-UTR deletion mutations is presented below in Table 2.

Replacement of the 3'-UTR of a Dengue Virus of a First Serotype with the 3'-UTR from a Dengue Virus of a Second Serotype Using the second approach, the 3'-UTR of rDEN3 may be replaced with the 3'-UTR of rDEN4, optionally containing the Δ30 mutation and nucleotides additional to the Δ30 mutation deleted from the 3'-UTR. Other examples include replacement of the 3'-UTR of rDEN3 with the 3'--UTR of dengue virus serotypes 1 and 2, optionally containing the Δ30 mutation and nucleotides additional to the Δ30 mutation deleted from the 3'-UTR. Other examples include: replacement of the 3'-UTR of rDEN1with the 3'-UTR of dengue virus serotypes 2, 3, and 4, optionally containing the Δ30 mutation and nucleotides additional to the Δ30 mutation deleted from the 3'-UTR; replacement of the 3'-UTR of rDEN2 with the 3'-UTR of dengue virus serotypes 1, 3, and 4, optionally containing the Δ30 mutation and nucleotides additional to the Δ30 mutation deleted from the 3'-UTR; and, replacement of the 3'-UTR of rDEN4 with the 3'-UTR of dengue virus serotypes 1, 2, and 3, optionally containing the Δ30 mutation and nucleotides additional to the Δ30 mutation deleted from the 3'-UTR.

Embodiments that involve replacement of the 3'-UTR of a dengue virus of a first serotype with the 3'-UTR of dengue virus of a second serotype include:

a) rDEN1-3'D2, rDEN1-3'172x, rDEN1-3'D3, rDEN1-3'D3x, rDEN-3'D4, rDEN1-3'D4x;
rDEN1/2-3'D1, rDEN1/2-3'1)1x, rDEN1/2-3'D3, rDEN1/2-3'D3x, rDEN1/2-3'D4, rDEN1/2-3'D4x;
rDEN1/3-3'D3, rDEN1/3-3'D1x, rDEN1/3-3'D2, rDEN1/3-3'D2x, rDEN1/3-3'D4, rDEN1/3-3'D-4x;
rDEN1/4-3'D1, rDEN1/4-3'D1x, rDEN1/4-3'D2, rDEN1/4-3'D2x, rDEN1/4-3'D3, rDEN1/4-3'D3x;

b) rDEN2-3'D1, rDEN2-3'D1x, rDEN2-3'D3, rDEN2-3'D3x, rDEN2-3'D4, rDEN2-3'D4x;
rDEN2/1-3'D2, rDEN2/1-3'12x, rDEN 2/1-3'D3, rDEN2/1-3'D3x, rDEN2/1-3'D4, rDEN2/1-3'D4x;
rDEN2/3-3'D1, rDEN2/3-3'D1x, rDEN2/3-3'D2, rDEN2/3-3'D2x, rDEN2/3-3'D4, rDEN2/3-3D4x;
rDEN2/4-3'D1, rDEN2/4-3'D1x, rDEN2/4-3'D2, rDEN214-3'D2x, rDEN2/4-3'D3, rDEN2/4-3'D3x;

c) rDEN3-3'D1, rDEN3-3'D1x, rDEN3-3'D2, rDEN3-3'D2x, rDEN3-3'D4, rDEN3-3'134x;
rDEN3/1-3'D2, rDEN3/1-3'D2x, rDEN311-3'D3, rDEN3/1-3'D3x, rDEN3/1-3'D4, rDEN3/1-3' D4x;
rDEN3/2-3'M rDEN3/2-3'D1x, rDEN3/2-3'D3, rDEN3/2-3'D3x, rDEN3/2-3'D4, rDEN3/2-3'D4x;
rDEN3/4-3'D1, rDEN3/4-3'D1x, rDEN3/4-3'D2, rDEN3/4-3'12x, rDEN3/4-31)3, rDEN3/4-3'D3x; and d) rDEN4-3'1, rDEN4-3'131x, rDEN4-3'D2, rDEN4-3"D2x, rDEN4-3'D3, rDEN4-31)3x;
rDEN4/1-3' D2, rDEN4/1-3'D2x, rDEN4/1-3'D3, rDEN4/1-3'D3x, rDEN4/1-3'D4, rDEN4/1-3'1)4x;
rDEN4/2-3'D1, rDEN4/2-3'D x, rDEN4/2-3'D3, rDEN4/2-3'D3x, rDEN4/2-3'D4, rDEN4/2-3'D4x;
rDEN4/3-3'D1, rDEN4/3-3'D1x, rDEN4/3-3'D2, rDEN413-3'D2x, rDEN4/3-3'D4, rDEN4/3-3'D4x;

where x is a mutation listed in Table 2.

Method of Making and Using Dengue or Chimeric Dengue Viruses

The viruses (including chimeric viruses) of the present invention can be made using standard methods in the art. For example, an RNA molecule corresponding to the genome of a virus can be introduced into host cells, e.g., Vero cells, from which (or the supernatants of which) progeny virus can then be purified. In this method, a nucleic acid molecule (e.g., an RNA molecule) corresponding to the genome of a virus is introduced into the host cells, virus is harvested from the medium in which the cells have been cultured, and the virus is formulated for the purposes of vaccination.

The viruses of the invention can be administered as primary prophylactic agents in adults or children at risk of infection, or can be used as secondary agents for treating infected patients. For example, in the case of DEN virus and chimeric DEN viruses, the vaccines can be used in adults or children at risk of DEN virus infection, or can be used as secondary agents for treating DEN virus-infected patients. Examples of patients who can be treated using the DEN virus--related vaccines and methods of the invention include (i) children in areas in which DEN virus is endemic, (ii) foreign travelers, (iii) military personnel, and (iv) patients in areas of a DEN virus epidemic. Moreover, inhabitants of regions into which the disease has been observed to be expanding (e.g., beyond Sri Lanka, East Africa and Latin America), or regions in which it may be observed to expand in the fixture can be treated according to the invention.

Formulation of the viruses of the invention can be carried out using methods that are standard in the art. Numerous pharmaceutically acceptable solutions for use in vaccine preparation are well known and can readily be adapted for use in the present invention by those of skill in this art (see, e.g., Remington's Pharmaceutical Sciences (18th edition), ed. A. Gennaro. 1990, Mack Publishing Co., Easton, PA). The viruses can be diluted in a physiologically acceptable solution, such as sterile saline, sterile buffered saline, or L-15 medium. In another example, the viruses can be administered and formulated, for example, as a fluid harvested from cell cultures infected with dengue virus or chimeric dengue virus.

The vaccines of the invention can be administered using methods that are well known in the art, and appropriate amounts of the vaccines administered can readily he determined by those of skill in the art. For example, the viruses of the invention can he formulated as sterile aqueous solutions containing between $10^2$ and $10^7$ infectious units (e.g., plaque-forming units or tissue culture infectious doses) in a dose volume of 0.1 to 1.0 ml, to be administered by, for example, intramuscular, subcutaneous, or intradermal routes. Further, the vaccines of the invention can be administered in a single dose or, optionally, administration can involve the use of a priming dose followed by a booster dose that is administered, e.g., 2-6 months later, as determined to be appropriate by those of skill in the art.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), inuramyl dipeptide, monophosphoryl lipid A, or polyphosphazine. Although these adjuvants are typically used to enhance immune responses to inactivated vaccines, they can also be used with live vaccines.

Nucleic Acid Sequences

Nucleic acid sequences of DEN viruses are useful for designing nucleic acid probes and primers for the detection of deletion or chimeric 3'-UTRs in a sample or specimen with high sensitivity and specificity. Probes or primers corresponding to deletion or chimeric 3'-UTRs can be used to detect the presence of deletion or chimeric 3'-UTRs in general in the sample, to quantify the amount of deletion or chimeric 3'-UTRs in the sample, or to monitor the progress of therapies used to treat DEN virus infection. The nucleic acid and corresponding amino acid sequences are useful as laboratory tools to study the organisms and diseases and to develop therapies and treatments for the diseases.

Nucleic acid probes and primers selectively hybridize with nucleic acid molecules encoding deletion or chimeric 3'-UTRs or complementary sequences thereof. By "selective" or "selectively" is meant a sequence which does not hybridize with other nucleic acids to prevent adequate detection of the deletion or chimeric 3-UTRs. Therefore, in the design of hybridizing nucleic acids, selectivity will depend upon the other components present in the sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus has the same meaning as "specifically hybridizing." The selectively hybridizing nucleic acid probes and primers of this invention can have at least 70%, 80%, 85%, 90%, 95%, 97%, 98% and 99% complementatity with the segment of the sequence to which it hybridizes, preferably 85% or more.

The present invention also contemplates sequences, probes and primers that selectively hybridize to the encoding nucleic acid or the complementary, or opposite, strand of the nucleic acid. Specific hybridization with nucleic acid can occur with minor modifications or substitutions in the nucleic acid, so long as functional species-species hybridization capability is maintained. By "probe" or "primer" is meant nucleic acid sequences that can be used as probes or primers for selective hybridization with complementary nucleic acid sequences for their detection or amplification, which probes or primers can vary in length from about 5 to 100 nucleotides, or preferably from about 10 to 50 nucleotides, or most preferably about 18-24 nucleotides. Isolated nucleic acids are provided herein that selectively hybridize with the species-specific nucleic acids under stringent conditions and should have at least five nucleotides complementary to the sequence of interest as described in *Molecular Cloning: A Laboratory Manual*, 2 nd ed., Sambrook, Fritsch and Mardatis, Cold Spring Harbor Laboratory, Cold Spring Harbor, NY, 1989.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of detecting the presence of deletion or chimeric 3'-UTRs, the degree of complementarity between the hybridizing nucleic acid (probe or primer) and the sequence to which it hybridizes is at least enough to distinguish hybridization with a nucleic acid from other organisms.

The nucleic acid sequences of the invention include a diagnostic probe that serves to report the detection of a cDNA amplicon amplified from the viral genomic RNA template by using a reverse-transeription/polymerase chain reaction (RT-PCR), as well as forward and reverse amplimers that are designed to amplify the cDNA amplicon. In certain instances, one of the amplimers is designed to contain a vaccine virus-specific mutation at the 3'-terminal end of the arnplimer, which effectively makes the test even more specific for the vaccine strain because extension of the primer at the target site, and consequently amplification, will occur only if the viral RNA template contains that specific mutation.

Automated PCR-based nucleic acid sequence detection systems have been recently developed. TaqMari assay (Applied Biosystems) is widely used. A more recently developed strategy for diagnostic genetic testing makes use of molecular beacons (Tyagi and Kramer 1996 *Nature Biotechnology* 18:303-308). Molecular beacon assays employ quencher and reporter dyes that differ from those used in the TaqMan assay. These and other detection systems may be used by one skilled in the art.

Dengue Virus Type 3 (DEN3) Vaccine Components Generated by Introduction of Deletions in the 3' Untranslated Region (UTR) or Exchange of the DEN3 3'-UTR with that of DEN4

There are four dengue virus serotypes (DEN1, DEN2, DEN3, and DEN4) which circulate in tropical and subtropical regions of the world inhabited by more than 2.5 billion people (Gubler D J 1998 *Clin Microbiol Rev* 11:480-496). DEN viruses are endemic in at least 100 countries and cause more human disease than any other arbovirus. Annually, there are an estimated 50-100 million dengue infections and hundreds of thousands of cases of dengue hemorrhagic fever/ shock syndrome (DHF/DSS), with children bearing much of the disease burden (Gubler D J and Meltzer M 1999 *Adv Virus Res* 53:35-70). DHF/DSS remains a leading cause of hospitalization and death of children in at least eight southeast Asian countries (World Health Organization 1997 *Dengue Haemorrhagic Fever: Diagnosis, Treatment, Prevention and Control, 2nd edition*, WHO, Geneva). The dramatic increase in both the incidence and severity of disease caused by the four DEN serotypes over the past two decades is due in large part to the geographic expansion of the mosquito vectors, *Aedes aegypti* and *Aedes albopicius*, and the increased prevalence of the four DEN serotypes (Gubler D J 1998 *Clin Microbial Rev* 11:480-496). The dengue viruses are maintained in a life cycle of transmission from mosquito to human to mosquito with no other apparent viral reservoir participating in ibis life cycle in urban settings (Rice C M, 1996 in *Flaviviridae: The viruses and their replication*, Fields R N, Knipe D M, Howley P M, Chanock R M, Melnick J L., Monath T P, Roizman B, Straus S E, eds. Fields Virology. Philadelphia: Lippincott-Raven Publishers, pp. 931-959).

The DEN viruses, members of the Flaviviridae Easily, have spherical virions of approximately 40 to 60 Fier, which contain a single-stranded positive-sense RNA genome. A single polypeptide is co-translationally processed by viral and cellular proteases generating three structural proteins (capsid C, membrane M, and envelope E) and at least seven non-structural (NS) proteins. The genome organization of the DEN viruses is 5% UTR-C-prM-E-NS1-NS2A-NS2B-NS3-NS4A-NS4B-NS5-UTR-3 (UTR-untranslated region, prM-membrane precursor) (Rice C M, 1996 in *Flaviviridae: The viruses and their replication*, Fields B N, Knipe D M, Howley P M, Chanock R M, Melnick J L, Monath T P, Roizman B, Straus S E, eds. Fields Virology. Philadelphia: Lippincott-Raven Publishers, pp. 931-959).

In response to the increasing incidence and severity of DEN infection, development of vaccines is being pursued to prevent DEN virus disease. An economical vaccine that prevents disease caused by the DEN viruses has become a global public health priority. The cost-effectiveness, safety, and long-term efficacy associated with the live attenuated vaccine against yellow fever (YE) virus, another mosquito-borne flavivirus, serves as a model for the feasibility of developing of a live attenuated DEN virus vaccine (Monath T P, 1999 in *Yellow fever*, Plotkin S A, Orenstein W A, eds. Vaccines, Philadelphia: W. B. Saunders Co., 815-879). Additionally, an effective live attenuated Japanese encephalitis (JE) virus vaccine is used in Asia, and inactivated virus vaccines are available for JE and tick-borne encephalitis virus. The need for a vaccine against the DEN viruses is mounting, and, despite much effort, the goal of developing a safe and efficacious DEN virus vaccine has yet to be attained. An effective DEN virus vaccine must confer protection from each serotype, because all four serotypes commonly circulate in endemic regions and secondary infection with a heterologous serotype is associated with increased disease severity.

We have employed two strategies for generating live attenuated vaccine components against each serotype that can then be combined into tetravalent formulations (Blaney J E et al. 2006 *Viral Immunol.* 19:10-32). First, reverse genetics has been used to introduce an attenuating 30 nucleotide deletion (Δ30) mutation into the 3'-UTR of (DNA clones of each DEN serotype (Durbin, A P et al. 2001 *Am J Trap Med Hyg* 65:405-413; Whitehead S S et al. 2003 *J Virol*

77:1653-1657; Blaney J E et al. 2004 *Am J Trop Med Hyg* 71:811-821; Blaney J E et al 2004 *BMC Inf Dis* 4:39). Initially, the rDEN4Δ30 vaccine component was found to be attenuated in rhesus monkeys (Table 1) and phase I/II clinical trials in humans have demonstrated that virus infection results in low viremia, is strongly immunogenic, and exhibits minimal reactogenicity with no observation of serious adverse events (Durbin, A. P. et al, 2001 *Am J Trop Med Hyg* 65:405-413; Durbin et al. 2005 *J Inf Dis* 191:710-718), Recently, the rDEN1Δ30 vaccine component, which was also attenuated in rhesus monkeys (Table 1), has, been found to share a similar phenotype in clinical trials as that observed for rDEN4Δ30; low viremia, strong immunogenicity; and minimal reactogenicity in 20 volunteers (Whitehead S S et al. 2003 J Virol 77:1653-1657; Blaney J E et al. 2006 Viral Immunol. 19:10-32). Unfortunately, the rDEN2Δ30 and rDEN3Δ30 vaccine components did not appear to be satisfactorily attenuated in rhesus monkeys during pre-clinical testing and there is no plan to test these in humans (Table 1) (Blaney J E et al. 2004 *Am J Trop Med Hyg* 71:811-821; Blaney J E et al. 2004 *BMC Inf Dis* 4:39). Consequently, an alternative strategy for vaccine development has been generation of antigenic chimeric viruses by replacement of structural proteins of the attenuated rDEN4Δ30 vaccine component with those from DEN2 or DEN3 yielding the rDEN2/4Δ30 and rDEN3/4Δ30 vaccine components, respectively (Whitehead S S et al. 2003 *Vaccine* 21:4307-4316; Blaney J E et al. 2004 *Am Trop Med Hyg* 71:811-821). The rDEN2/4Δ30 vaccine virus has been tested in humans and appears safe and strongly immunogenic, while clinical evaluation of the rDEN3/4Δ30 virus is currently planned.

Here, we describe novel vaccine components for the DEN3 serotype generated by genetic modification of the 3'-UTR of the DEN3 cDNA clone (Blaney J E et al. 2004 *Am J Trop Med Hyg* 71:811-821). Development of these DEN3 vaccine components, which possess the full complement of wild type DEN3 proteins, is :important for two reasons. First, the present vaccine component for DEN3, rDEN3/4Δ30, may be found to be under- or over-attenuated in clinical trials. Second, an optimal vaccine for conferring protection from disease caused by DEN3 may require induction of T cell responses against the entire set of DEN3 proteins, rather than just the M and E which are the only DEN3 sequences present in the rDEN3/4Δ30 chimeric virus. To generate additional DEN3 vaccine components, novel deletions which encompass or border the Δ30 deletion in the 3'-UTR were introduced into the rDEN3 cDNA clone. Alternatively, the 3'-UTR of the rDEN3 cDNA clone was replaced with that of rDEN4 or rDEN4Δ30. Viable viruses were analyzed for attenuation phenotypes in tissue culture, SCID mice transplanted with HuH-7 cells, and rhesus monkeys. Three mutant viruses (rDEN3Δ30/31, rDEN3Δ86, and rDEN3-3'D4Δ30) have preclinical phenotypes which suggest they may be safe and immunogenic in humans.

Generation of rDEN3 Deletion Mutants

Figure 8:
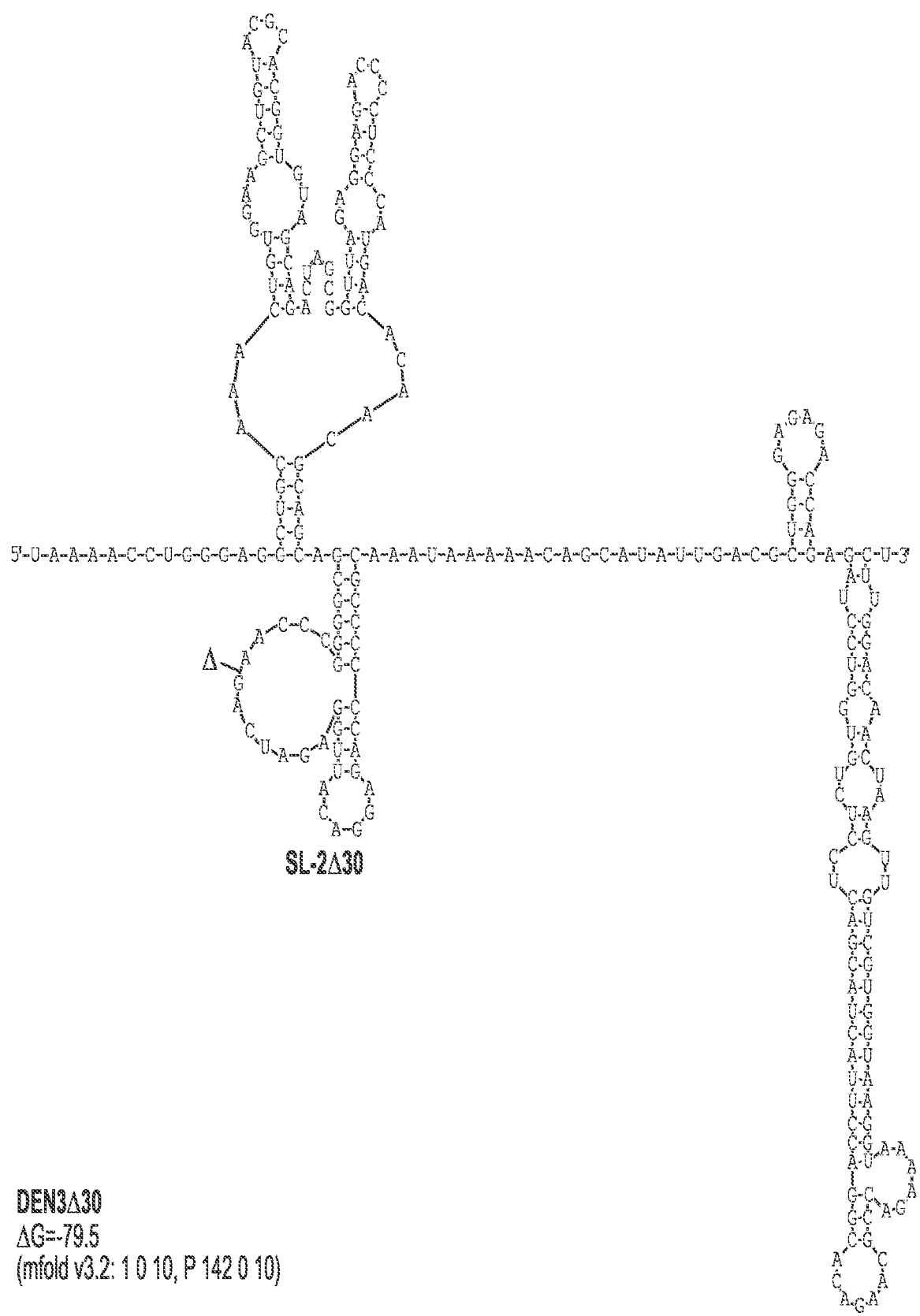
FIG. 8. Δ30 deletion mutation depicted for each of the dengue virus serotypes DEN1, DEN2, DEN3 and DEN4. The Δ30 mutation deletes nt 174 to 145 of DEN1, nt 173 to 144 of DEN2, nt 173 to 143 of DEN3, and nt 172 to 143 of DEN4, with reverse-direction numbering system. The deleted region is indicated by the Δ symbol. The nucleotide sequence shown in FIG. 8:—SEQ ID NO: 8.
Figure 9:
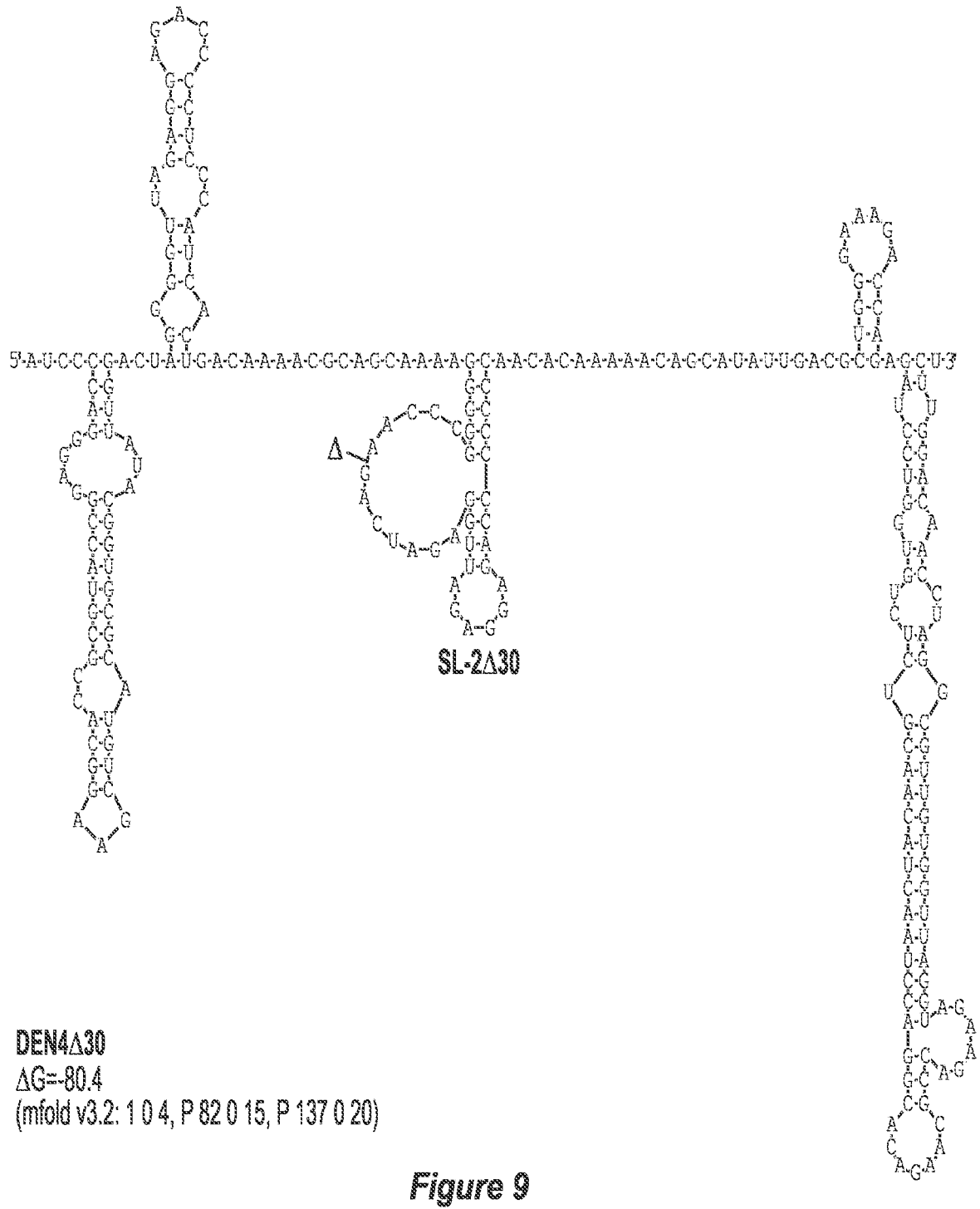
FIG. 9. Δ30 deletion mutation depicted for each of the dengue virus serotypes DEN1, DEN2, DEN3 and DEN4. The Δ30 mutation deletes nt 174 to 145 of DEN1, nt 173 to 144 of DEN2, nt 173 to 143 of DEN3, and nt 172 to 143 of DEN4, with reverse-direction numbering system. The deleted region is indicated by the Δ symbol. The nucleotide sequence shown in FIG. 9:—SEQ ID NO: 9.
Figure 10:
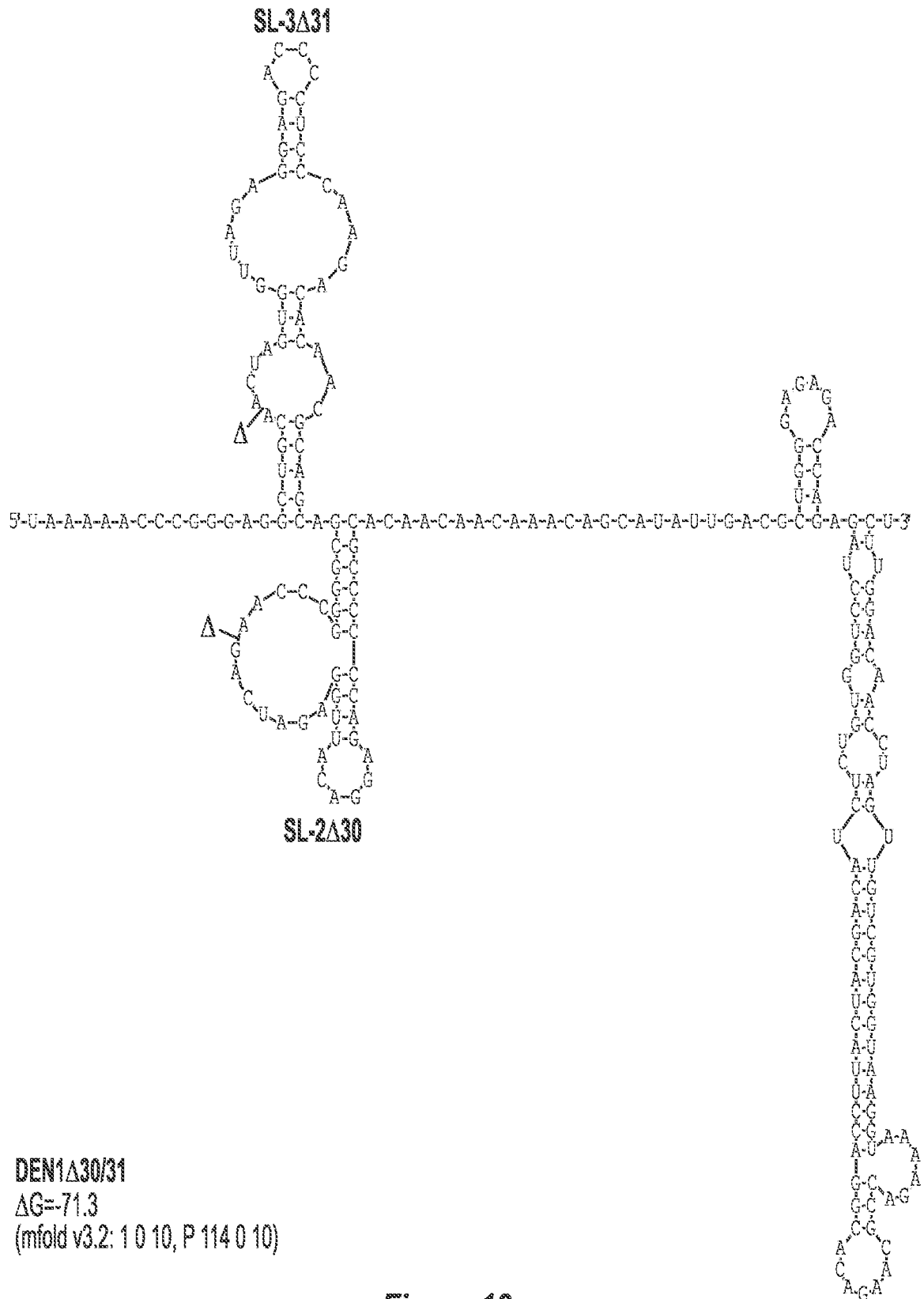
FIG. 10. Δ30/31 deletion mutation depicted for each of the dengue virus serotypes DEN1, DEN2, DEN3 and DEN4. In addition to the deletion of the nucleotides comprising the Δ30 mutation, the Δ31 mutation deletes nt 258 to 228 of DEN1, DEN2, DEN3, and DEN4, with reverse-direction numbering system. The deleted region is indicated by the Δ symbol. The nucleotide sequence shown in FIG. 10:—SEQ ID NO: 10.
Figure 11:
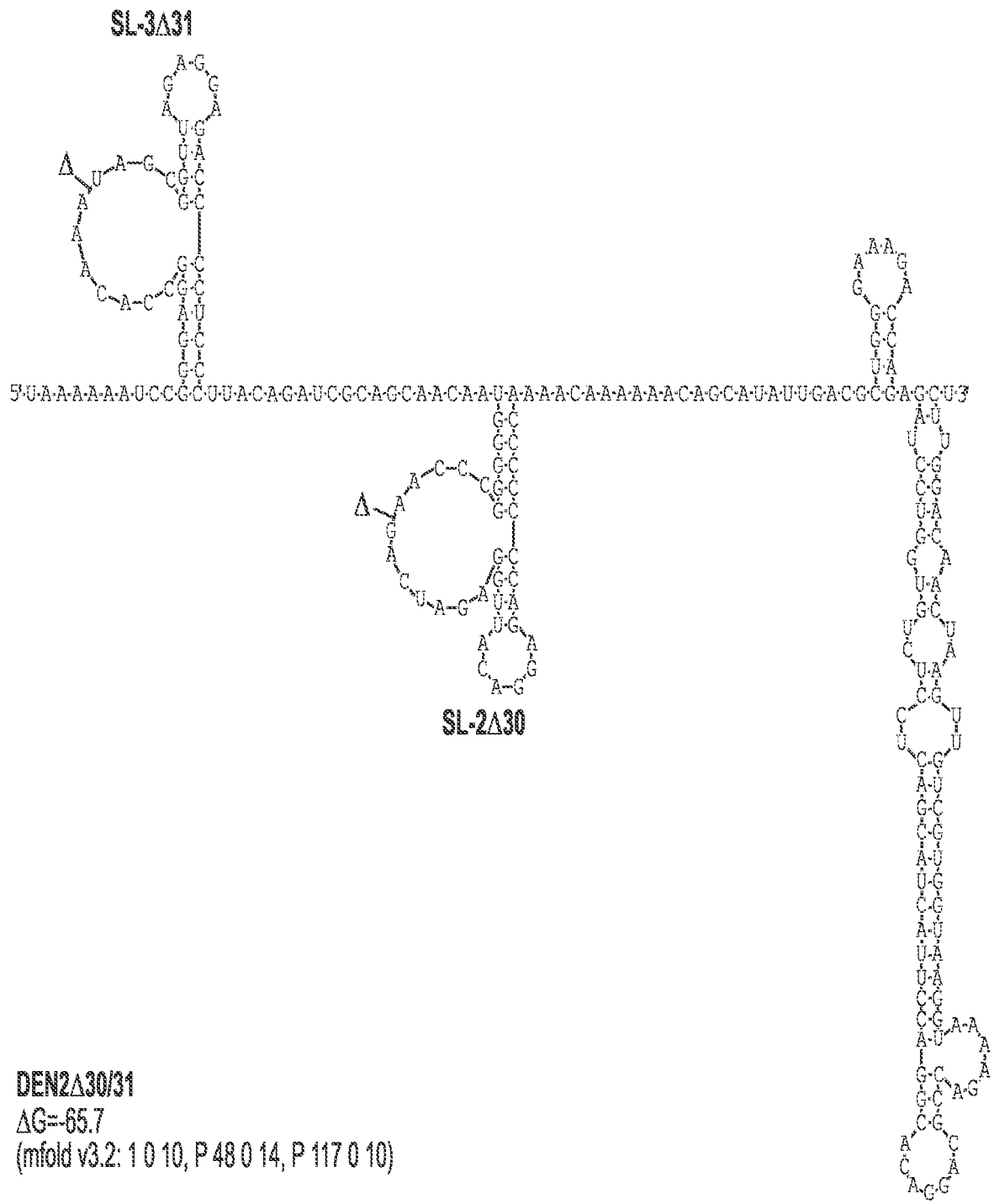
FIG. 11. Δ30/31 deletion mutation depicted for each of the dengue virus serotypes DEN1, DEN2, DEN3 and DEN4. In addition to the deletion of the nucleotides comprising the Δ30 mutation, the Δ31 mutation deletes nt 258 to 228 of DEN1, DEN2, DEN3, and DEN4, with reverse-direction numbering system. The deleted region is indicated by the Δ symbol. The nucleotide sequence shown in FIG. 11:—SEQ ID NO: 11.
Figure 12:
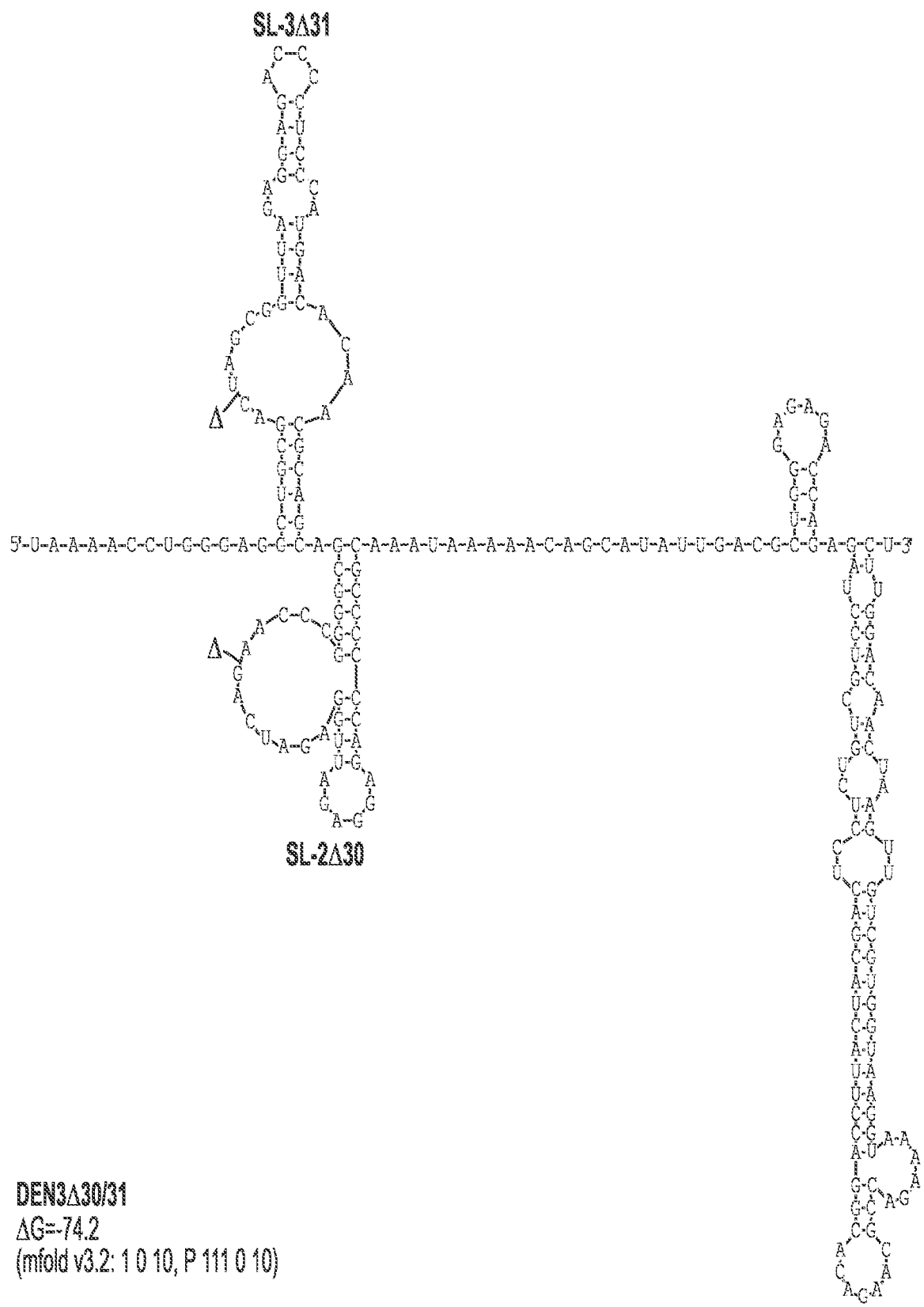
FIG. 12. Δ30/31 deletion mutation depicted for each of the dengue virus serotypes DEN1, DEN2, DEN3 and DEN4. In addition to the deletion of the nucleotides comprising the Δ30 mutation, the Δ31 mutation deletes nt 258 to 228 of DEN1, DEN2, DEN3, and DEN4, with reverse-direction numbering system. The deleted region is indicated by the Δ symbol. The nucleotide sequence shown in FIG. 12:—SEQ ID NO: 12.
Figure 14:
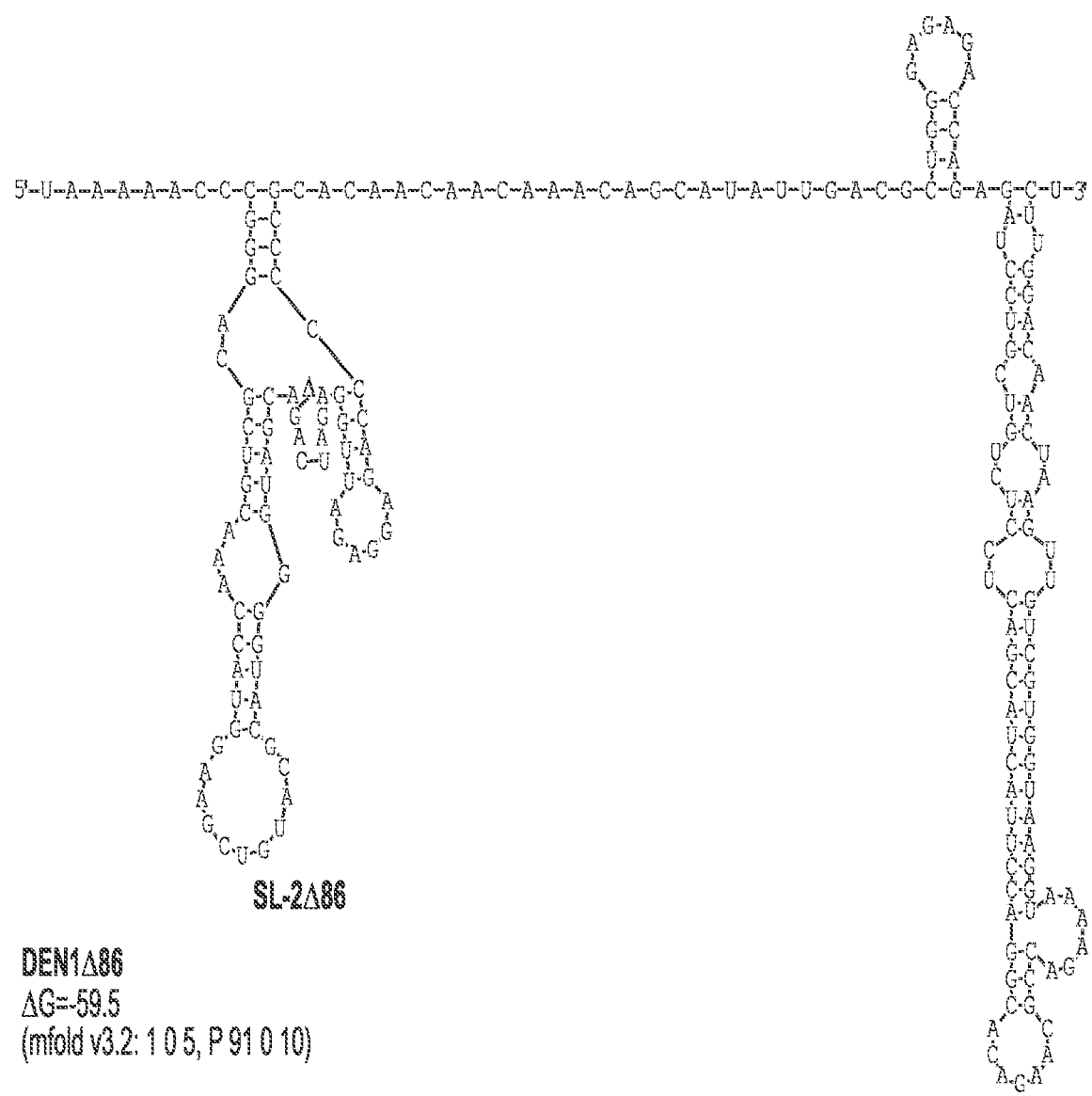
FIG. 14. Δ86 deletion mutation depicted for each of the dengue virus serotypes DEN1, DEN2, DEN3 and DEN4. The Δ86 mutation deletes nt 228 to 145 of DEN1, nt 228 to 144 of DEN2, nt 228 to 143 of DEN3, and nt 228 to 143 of DEN4, with reverse-direction numbering system. The deleted region is indicated by the Δ symbol. The nucleotide sequence shown in FIG. 14:—SEQ ID NO: 14.
Figure 15:
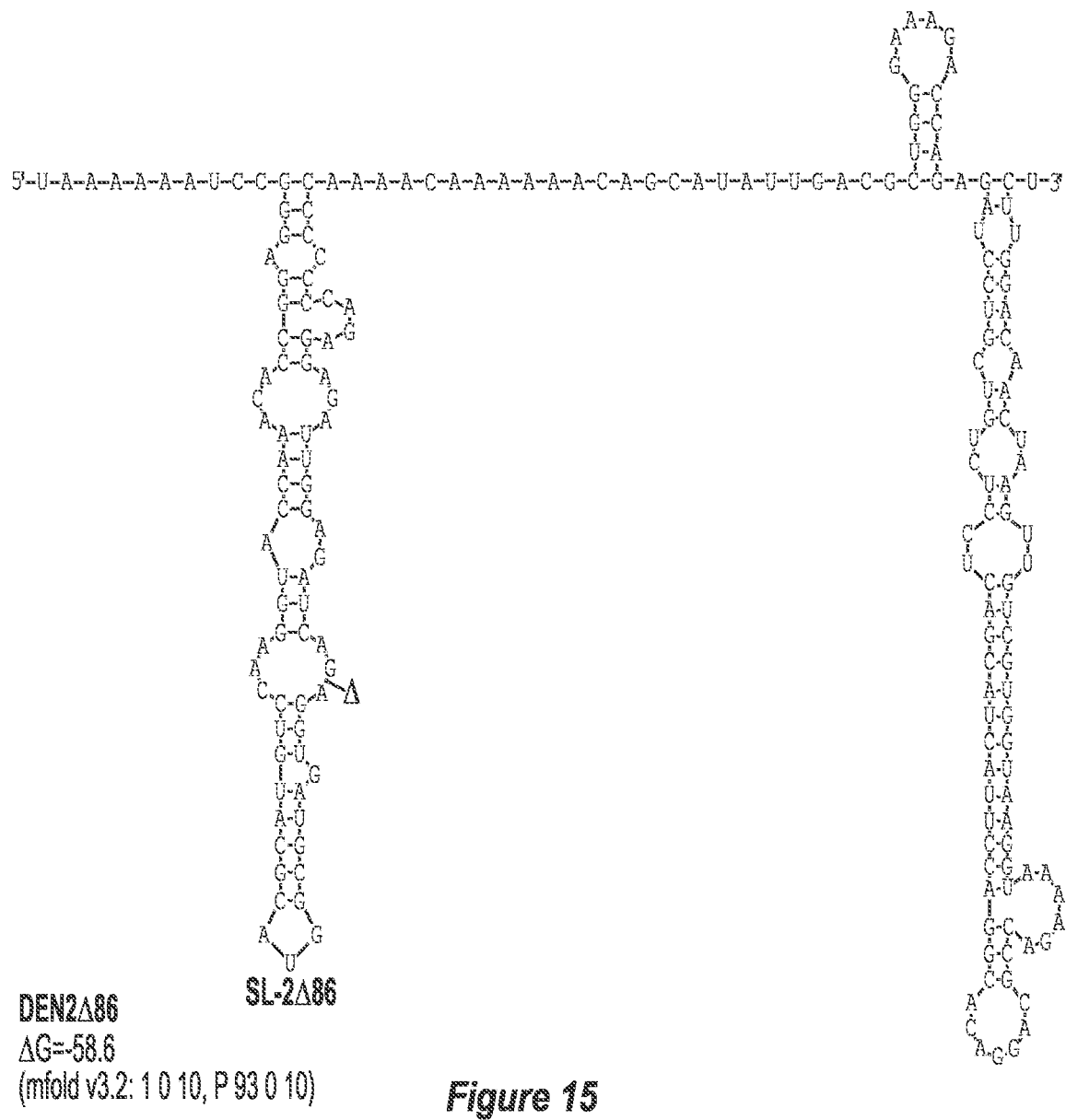
FIG. 15. Δ86 deletion mutation depicted for each of the dengue virus serotypes DEN1, DEN2, DEN3 and DEN4. The Δ86 mutation deletes nt 228 to 145 of DEN1, nt 228 to 144 of DEN2, nt 228 to 143 of DEN3, and nt 228 to 143 of DEN4, with reverse-direction numbering system. The deleted region is indicated by the Δ symbol. The nucleotide sequence shown in FIG. 15:—SEQ ID NO: 15.
Figure 16:
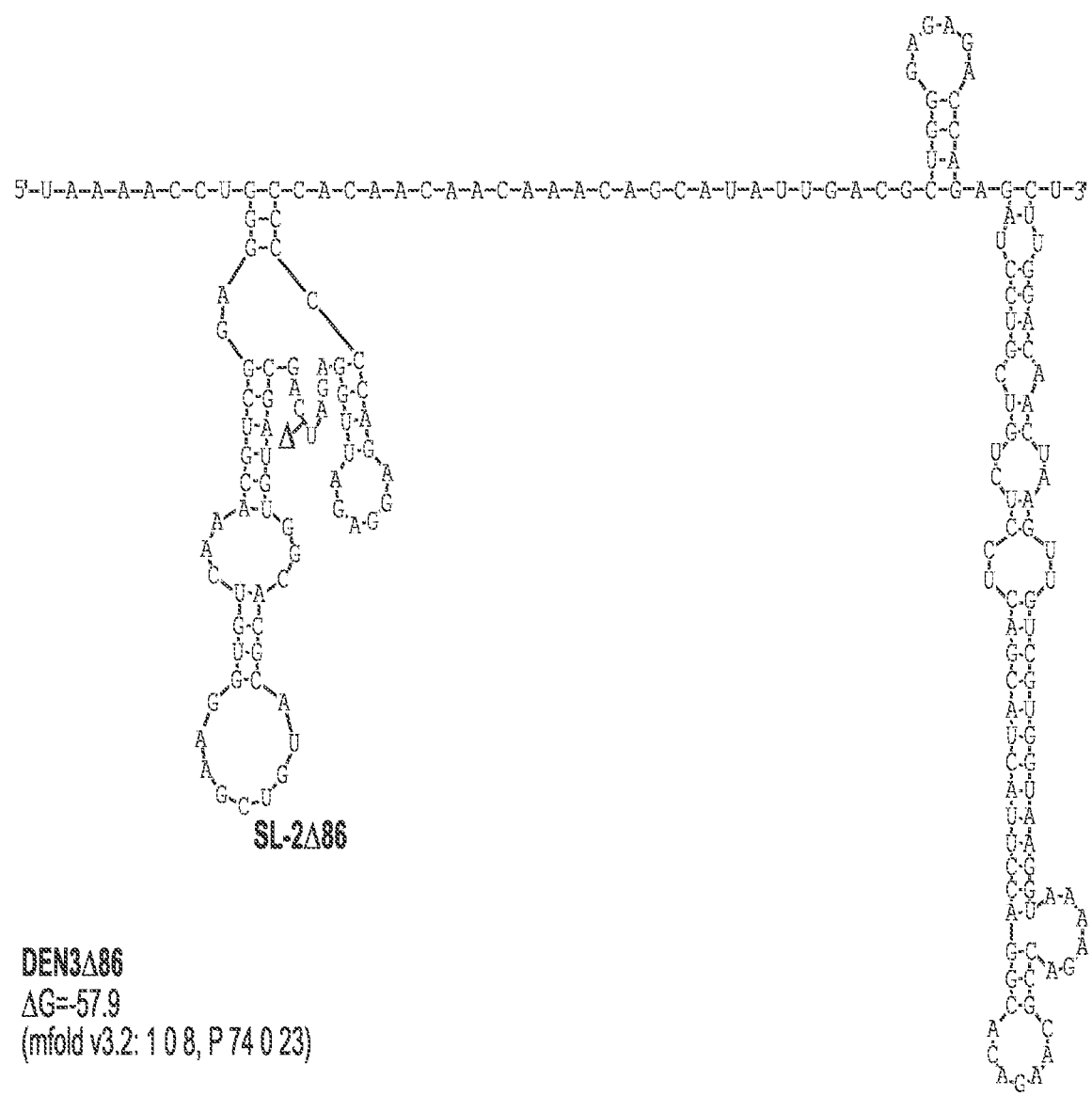
FIG. 16. Δ86 deletion mutation depicted for each of the dengue virus serotypes DEN1, DEN2, DEN3 and DEN4. The Δ86 mutation deletes nt 228 to 145 of DEN1, nt 228 to 144 of DEN2, nt 228 to 143 of DEN3, and nt 228 to 143 of DEN4, with reverse-direction numbering system. The deleted region is indicated by the Δ symbol. The nucleotide sequence shown in FIG. 16:—SEQ ID NO: 16.
Figure 17:
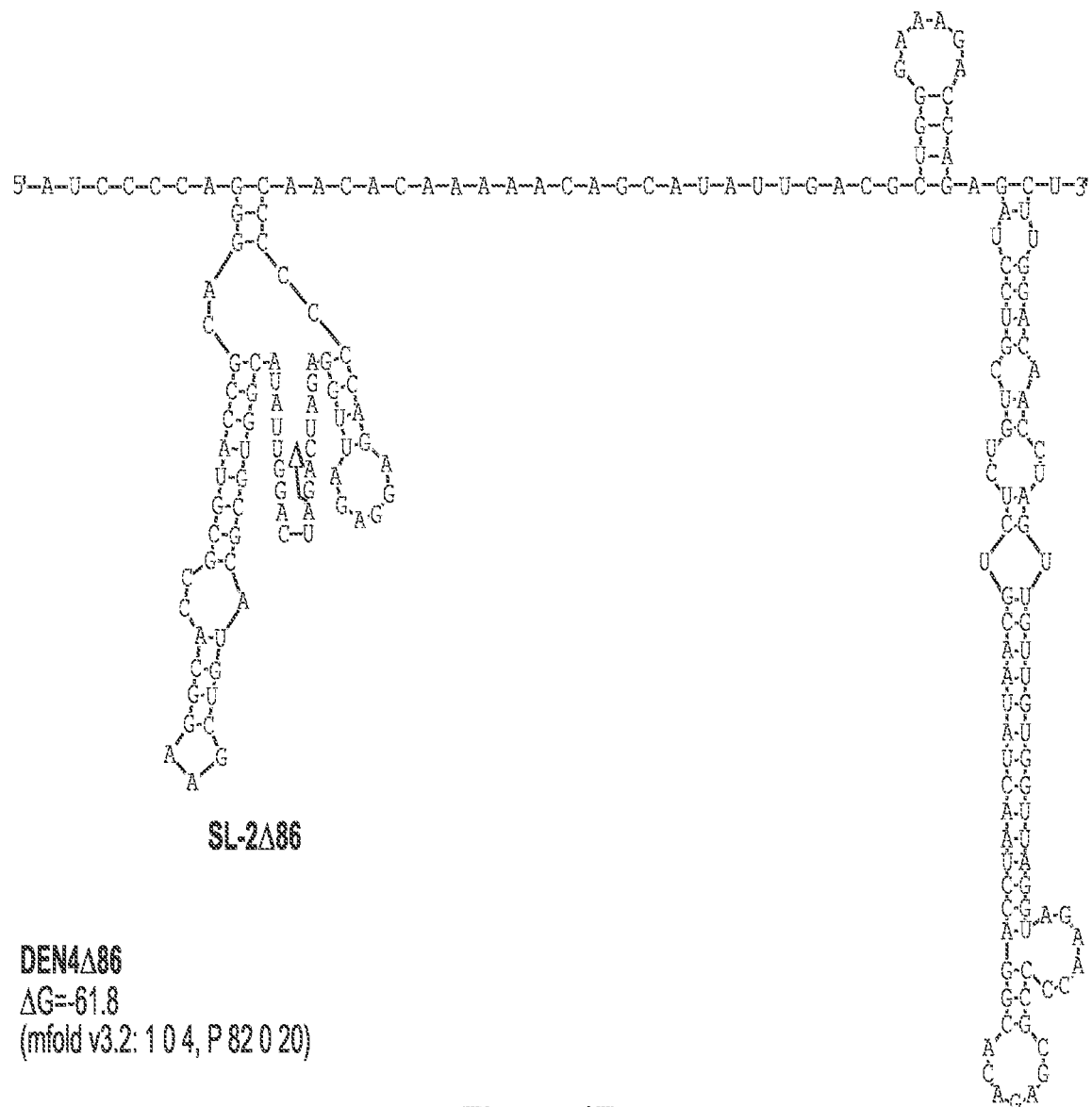
FIG. 17. Δ86 deletion mutation depicted for each of the dengue virus serotypes DEN1, DEN2, DEN3 and DEN4. The Δ86 mutation deletes nt 228 to 145 of DEN1, nt 228 to 144 of DEN2, nt 228 to 143 of DEN3, and nt 228 to 143 of DEN4, with reverse-direction numbering system. The deleted region is indicated by the Δ symbol. The nucleotide sequence shown in FIG. 17:—SEQ ID NO: 17.

We sought to generate expanded deletion mutations which include the original Δ30 (nt 173-143) mutation. Table 2 lists seven deletion mutations which encompass the original Δ30 mutation including Δ50, Δ61, Δ80, Δ86, Δ116A, Δ116B and Δ146. In addition, the Δ30/31 mutation includes the original Δ30 mutation and a non-contiguous 31 at deletion. The Δ31 mutation was also generated alone to discern the contribution of either Δ30 or Δ31 in the combined Δ30/31 deletion mutation. The location of bordering nucleotides of deletions in the predicted secondary structure of the DEN3 3'-UTR are indicated in FIG. 4. In addition, the predicted secondary structure of the DEN3 3'-UTR for rDEN3Δ30, rDEN3Δ30/31, and rDEN3Δ86 are indicated in FIGS. 8, 12, and 16, respectively.

TABLE 1

Effects of the Δ30 mutation on the four DEN serotypes in rhesus monkeys

| Virus | Viremia[a] | | | Geometric mean neutralizing antibody titer[b] | Reference |
| | % of viremic monkeys | Mean no. of viremic days per monkey | Mean peak virus titer (log10PFU/ml) ±SE) | | |
| --- | --- | --- | --- | --- | --- |
| rDEN1 | 100 | 2.8 | 2.1 ± 0.1 | 1,230 | Whitehead et al. |
| rDEN1Δ30 | 50 | 0.5 | 0.8 ± 0.1 | 780 | *J. Virol.*, 2003, 77: 1653 |
| rDEN2 | 100 | 4.0 | 1.9 ± 0.1 | 173 | Blaney et al. BMC |
| rDEN2Δ30 | 100 | 2.8 | 1.7 ± 0.2 | 91 | *Inf Dis.*, 2004, 4: 39 |
| rDEN3 | 100 | 2.3 | 1.4 ± 0.2 | 363 | Blaney et al. *Am. J.* |
| rDEN3Δ30 | 100 | 2.0 | 1.5 ± 0.2 | 265 | *Trop. Med. Hyg.*, 2004 71: 811 |
| rDEN4 | 100 | 3.0 | 2.2 ± 0.2 | 322 | Hanley et al. |
| rDEN4Δ30 | 100 | 2.0 | 1.4 ± 0.2 | 154 | *Vaccine*, 2004 22: 3440 |

[a]Groups of rhesus monkeys were inoculated subcutaneously with 5.0 log$_{10}$ PFU of the indicated virus in a 1 ml dose. Serum was collected daily for 10 days. Virus titer in serum was determined by plaque assay in Vero cells.
[b]Plaque reduction (60%) neutralizing antibody titers were determined on day 28 serum using indicated wild type virus. Reciprocal dilution of geometric mean is indicated.

TABLE 2

Deletion mutations created in the 3'-UTR of DEN3 Sleman/78

| Mutation | Deleted nucleotides[a] | Deletion junction |
| --- | --- | --- |
| Δ30 | 173-143 | -CCAAAGACU- |
| Δ31 | 258-228 | -CUGCAGACU- |

TABLE 2-continued

Deletion mutations created in the 3'-UTR of DEN3 Sleman/78

| Mutation | Deleted nucleotides[a] | Deletion junction |
|---|---|---|
| Δ50 | 192-143 | -CACAΔGACU- |
| Δ61 | 173-113 | -CCGAΔUAAA- |
| Δ80 | 192-113 | -CACAΔUAAA- |
| Δ86 | 228-143 | -UAGCΔGACU- |
| Δ116 (A) | 228-113 | -UAGCΔUAAA- |
| Δ116 (B) | 258-143 | -CUGCΔGACU- |
| Δ146 | 258-113 | -CUGCΔDAAA- |
| Δ30/31 | 173-143 | -CCAAΔGACU- |
|  | 258-228 | -CUGCΔGACU- |

[a]Numbering is from the 3'-end of viral genome

PCR mutagenesis was used to introduce the nine new deletion mutations into the DEN3 Sleman/78 cDNA plasmid, p3, which was previously used to generate the rDEN3Δ30 vaccine component (Blaney J E et al. 2004 *Am J Trop Med Hyg* 71:811-821). The p3-frag.4 cDNA subclone was used as the template for PCR reactions with indicated pairs of mutagenic oligonucleotides listed in Table 3, except for the Δ30/31 deletion mutation which used p3-frag.4Δ30 cDNA subclone as a template. PCR products were ligated and used to transform competent bacterial cells, Plasmid DNA was isolated from bacterial clones and the presence of the appropriate deletion mutation was confirmed by sequence analysis. To generate intact DEN3 cDNA plasmids containing the deletion mutations, the KpnI-PstI fragment (963 nt) from the mutated p3-frag.4 cDNA subclones were introduced into the p3-7164 cDNA plasmid. The p3-7164 plasmid encodes the 7164 Vero cell adaptation mutation which had previously been shown to enhance growth and transfection efficiency in Vero cells (Blaney J E et al. 2004 *Am J Trop Med Hyg* 71:811-821). Full length p3 plasmids containing the deletion mutations were confirmed to contain the correct 3'-UTR sequence. Mutations in addition to the engineered deletions were identified in the rDEN3Δ30/31 and rDEN3Δ86 viruses when compared to the DEN3 p3 plasmid cDNA (Genbank #AY656169) (Table 4).

TABLE 3

Mutagenic primer sequences for construction of 3'-UTR deletions

| Primer name | Sequence (5'→3') |
|---|---|
| 113F | TAAAAACAGCATATTGACGCTGGGAG (SEQ ID NO: 24) |
| 143F | GACTAGAGGTTAGAGGAGAC (SEQ ID NO: 25) |
| 228F | GACTAGCGGTTAGAGGAGACCCC (SEQ ID NO: 26) |
| 173R | TCGGGCCCCGCTGCTGCGTTG (SEQ ID NO: 27) |
| 173R (for Δ30) | TTGGGCCCCGCTGCTGCGTTG (SEQ ID NO: 28) |
| 192R | TGTGTCATGGGAGGGGTCCTC (SEQ ID NO: 29) |
| 228R | GCTACACCGTGCGTACAGCTTCC (SEQ ID NO: 30) |
| 258R | GCAGCCTCCCAGGTTTTACGTCC (SEQ ID NO: 31) |

TABLE 4

Mutations in addition to the engineered deletions that were identified in the rDEN3Δ30/31 and rDEN3Δ86 viruses when compared to the DEN3 p3 plasmid cDNA (Genbank # AY656169)

| Virus | Gene | Nucleotide position | Nucleotide substitution | Amino acid position | Amino acid change |
|---|---|---|---|---|---|
| rDEN3Δ30/31 | NS4B | 7164[a] | U→C | 115 | Val→Ala |
|  | NS4B | 7398 | C→U | 193 | Ala→Val |
| rDEN3Δ86 | M | 512 | A→G | 26 | Lys→Glu |
|  | NS3 | 6076 | C→U | 521 | silent |
|  | NS4B | 7164[a] | U→C | 115 | Val→Ala |
|  | NS5 | 8623 | U→C | 353 | silent |
|  | NS5 | 10267[b] | A→U | END | end→Tyr |
|  | 3'-UTR | 10455 | G→C | — | — |

[a]The 7164 mutation is a Vero cell adaptation mutation which was engineered into the cDNA construct.
[b]There is a mixed population at this nt position (A→A/U) that changes the stop codon (UAA) at the end of NS5 to UAU which encodes Tyr. This would serve to extend NS5 by 2 amino acids (Tyr-Thr-End) because a stop codon remains at nts 10271-10273.

For recovery of viruses, 5'-capped RNA transcripts were synthesized in vitro from cDNA plasmids and transfected into either Vero cells or C6/36 cells. Prior to transcription and generation of infectious virus, the linker sequences were removed from cDNA plasmids by digestion with SpeI. Plasmids were then recircularized by ligation, linearized with Acc651 (isoschizomer of KpnI which cleaves leaving only a single 3' nucleotide), and transcribed in vitro using SP6 polymerase. Purified transcripts were then transfected into Vero or C6/36 cells.

Recombinant viruses encoding each of the nine mutations, Δ30/31, Δ31, Δ50, MI, Δ80, Δ86, Δ116A, Δ146, were successfully recovered in C6/36 cells, while only rDENΔ31 was recovered in Vero cells. The rDEN3 deletion mutant viruses were then passaged once in Vero cells followed by biological cloning by two terminal dilutions in Vero cells. Cloned viruses were then passaged two to seven times in Vero cells in an attempt to reach a stock titer of at least 6.0 log$_{10}$PFU/ml which is considered sufficient to allow for cost-effective manufacture. Three recombinant viruses (rDEN3Δ50, rDEN3Δ116A, and rDEN3Δ146) were found to be excessively restricted for replication in Vero cells, despite being viable. Therefore, these three viruses were not studied further. The genetic sequence of the 3'-UTR was determined for the six remaining deletion mutant viruses that reached peak virus titers of at least 6.0 log₁₀PFU/ml The correct 3'-UTR sequence with the appropriate deletion was found for rDEN3Δ61, rDEN3Δ80, rDEN3Δ86 and rDEN3Δ30/31. However, two mutant viruses were found to contain additional deletions or mutations and were deemed to potentially have unstable genotypes. First, rIDEN3Δ31 had the correct 3'-UTR deletion of nt 258-228 but also contained a 25 nt deletion of nt 222-198. Second, rDEN3Δ116B had the correct 3'-UTR deletion ant 258-143 butt also contained a 8 nt deletion of nt 430-423 and a single A->G substitution at nt 265. The potential of genetic instability with these viruses precludes their use as vaccine components so they were not further studied. Therefore, of the nine original deletions constructed, four mutant viruses were found to replicate efficiently in Vero cells and were studied further; rDEN3Δ61, rDEN3Δ80, rDEN3Δ86 and rDEN3Δ30/31.

Generation of rDEN3 Chimeric Viruses with the 3'-UTR Derived from rDEN4 or rDEN4Δ30

Figure 18:
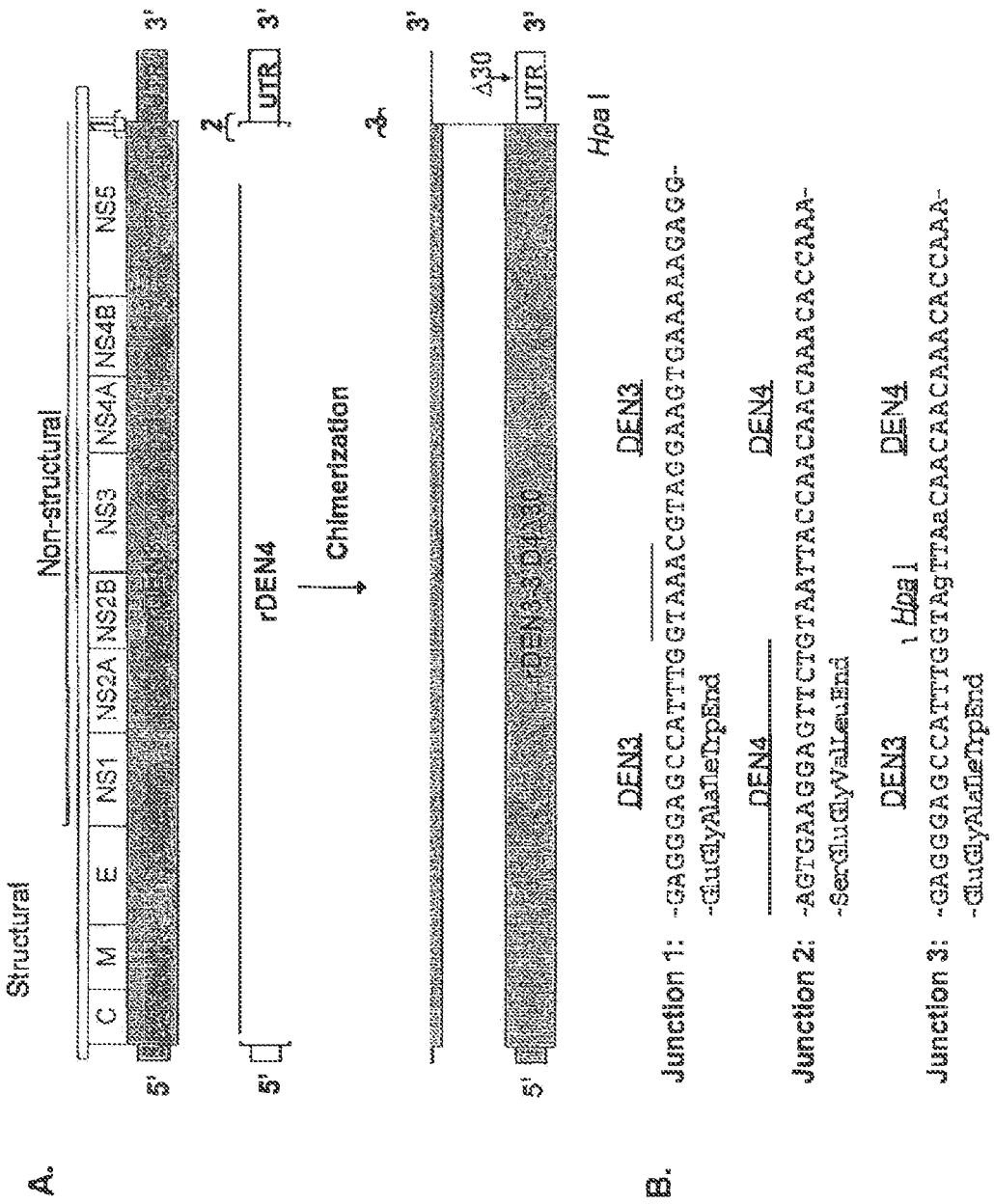
FIG. 18. Chimerization of rDEN3 with the rDEN4 or rDEN4 Δ3( )3'-UTR. A) recombinant 3'-UTR chimeric dengue viruses were constructed by replacing the 3'-urR of rDEN3 with regions derived from either rDEN4 or rDEN4 Δ30. The relative location of the Δ30 mutation in the 3'-UTR is indicated by an arrow. The junctions between the ORF and UTR for rDEN3 and rDEN4 are indicated as junctions 1 and 2, respectively. Intertypic junction 3 is also indicated for the resulting chimeric viruses. B) nucleotide and amino acid sequence of the junction regions are shown. For junction 3, nucleotide substitutions used to introduce a unique hpai restriction enzyme recognition site are shown in lower case. Junction 1—SEQ ID NOS: 18 (nucleotide) and 19 (amino acid); junction 2—SEQ ID NOS: 20 (nucleotide) and 21 (amino acid); junction 3—SEQ NOS: 22 (nucleotide) and 23 (amino acid).

Another strategy was employed to generate novel rDEN3 vaccine components; replacement of the 3'-UTR of the rDEN3 cDNA clone with that of rDEN4 or rDEN4Δ30 (FIG. 18A). The 3'-UTR chimeric virus, rDEN3-3'D4Δ30, was designed to be a vaccine component for inclusion in tetravalent formulations which share the Δ30 deletion mutation among all four serotypes. The rDEN3-3'D4 virus was designed to discern the contribution of the 3'-UTR cliimerization and the Δ30 mutation to any observed phenotypes.

The p3-3'D4Δ30 plasmid was generated as thllows. First, PCR mutagenesis was used to introduce a HpaI restriction site into the p3-frag.4 cDNA subclone (FIG. 18B). PCR products were ligated and used to transform competent bacterial Plasmid DNA was isolated from bacterial clones and the presence of the appropriate deletion mutation was confirmed by sequence analysis. To introduce the rDEN4Δ30 3'-UTR into the p3-.frag.4(HpaI) cDNA subclone, a 364 nt fragment encompassing the p4Δ30 3'-UTR was amplified by PCR using a forward primer (5'-AACAACAACAAACACCAAAGGCTATTG-3', SEQ ID NO: 32) and reverse primer (5'-CC-TACCGGTACCAGAACCTGTtG-3', SEQ ID NO: 33). To generate the p3-frag.4-3'D4Δ30 cDNA subclone, the HpaI-KpnI fragment was removed from p3-frag.4(HpaI) and replaced with the p4Δ30 3'-UTR PCR fragment which had been cleaved by KpnI. The PdyI-KpnI fragment of p3-frag.4-3'D4Δ30 was introduced into the p3 plasmid to make the full length cDNA clone, p3-3'D4Δ30. The sequence of the 3'-UTR and N55 junction were confirmed to be correct.

To generate p3-3'D4, the 30 deleted nucleotides of the Δ30 deletion mutation were introduced into the p3-frag.4-3'D4Δ30 subclone. Briefly, the kflul---Kpni fragment of p3-frag,4-3"D4Δ30, which encompasses the Δ30 region, was replaced with the corresponding fragment of p4 to make the plasmid, p3-frag.4-3'D4. To generate a full length p3 genome, the PstI-KpnI fragment of p3 was replaced with the corresponding fragment of p3-frag.4-3'D4. The 3'-UTR sequence of the p3-3'D4 plasmid was determined to be correct and contained the missing 30 nt of the Δ30 mutation.

For recovery of viruses, 5'-capped RNA transcripts were synthesized in vitro from cDNA plasrands and transfected into either Vero cells or C6/36 cells. Prior to transcription and generation of infectious virus, the linker sequences were removed from cDNA plasmids by digestion with SpeI. Plasmids were then recircularized by ligation, linearized with Acc651 (isoschizomer of KpnI which cleaves leaving only a single 3' nucleotide), and transcribed in vitro using SP6 polymerase. Purified transcripts were then transfected into Vero or C6/36 cells.

rDEN3-3'D4 was recovered in C6/36 cells and Vero cells, while rDEN3-3'D4Δ30 could only be recovered in Vero cells. Mutant viruses were then passaged once in Vero cells followed by biological cloning by two terminal dilutions in Vero cells. rDEN3-3'D4 and rDEN3-3'D4Δ30 were then passaged four or six times in Vero cells, respectively. The genetic sequence of the NS5 — 3'-UTR junction and 3'-15fR was found to be correct for rDEN3-3'D4 and rDEN3-3'D4Δ30. Therefore, both viruses were studied further.

Mutations were also identified in the rDEN3-3'D4Δ30 virus compared to the DEN3 p3 plasmid cDNA clone (5'-UTR and genes) and DEN4 p4 eDNA clone (3'-lITR) (Table 5).

TABLE 5

Mutations in the rDEN3-3D4Δ30 virus compared to the DEN3 p3 plasmid cDNA clone (5'-UTR and genes) and DEN4 p4 cDNA clone (3'-UTR)

| Virus | Gene | Nucleotide position | Nucleotide substitution | Amino acid position | Amino acid change |
|---|---|---|---|---|---|
| rDEN3-3'D4Δ30 | C | 250 | U → C | 52 | silent |
| | NS3 | 5899 | U → C | 462 | silent |
| | NS4B[a] | 7164 | U → C | 115 | Val → Ala |
| | 3'-UTR | 10534 | A → G | — | — |

[a]The 7164 mutation is a Vero cell adaptation mutation which was engineered into the cDNA construct.

Replication of DEN3 Mutant Viruses in SCID-HuH-7 Mice

The four deletion mutant viruses (rDEN3Δ30/31, rDEN3Δ61, rDEN3Δ80, and rDEN3686) which were found to replicate to high titer in Vero cells and were confirmed to have the correct 3'-UTR sequence and the rDEN3-3'D4 and rDEN3-3'D4Δ30 viruses were first evaluated in SCID-HuH-7 mice. The rDEN3-3'D4 and rDEN3-3'D4Δ30 were compared to determine the effect on replication of the 3'-UTR chimerization and any further attenuation conferred by the Δ30 mutation. SCID-HuH-7 mice contain solid tumors of the HuH-7 human hepatoma cell line, and analysis of virus replication in this mouse model serves as a surrogate for DEN virus replication in the human liver. Numerous DEN virus mutant viruses have been identified by evaluation in SC1D-HuH-7 mice (Blaney J E et al. 2002 *Virology* 300:125-139; Hanley et al. 2004 *Vaccine* 22:3440-3448; Blaney J E et al. 2006 *Viral Immunol.* 19:10-32). This mouse model provided the original evidence that the rDEN3Δ30 virus was not attenuated compared to parent virus rDEN3, while the antigenic chimeric virus, rDEN3/4Δ30, was approximately 100-fold restricted in replication in the SCID-Huff-7 mice when compared to wild type parent viruses (Blaney 1E et al. 2004 *Am J Trop Med Hyg* 71:811-821).

For analysis of virus replication in SCID-HuH-7 mice, four to six week-old SCID mice (Tac:Ier:Ha(ICR)-Prkdc$^{scid}$) (Taconic Farms) were injected intraperitoneally with 0.1 mL phosphate-buffered saline containing 10 7 HuH-7 cells which had been propagated in tissue culture. Tumors were detected in the peritoneum five to six weeks after transplantation, and tumor-bearing mice were infected by direct inoculation into the tumor with $10^4$ FEU of virus in 50 µl Opti-MEM I. Serum was collected from infected mice on day 7 post-infection and frozen at −80° C. The virus titer was determined by plaque assay in Vero cells.

As indicated in Table 6, wild type DEN3 Sleman/78 replicated to a mean peak virus titer of nearly $10^{6.9}$ PFU/ml. Although a decreased level of replication was observed fOr each of the six mutant viruses, the differences in replication were not statistically significant. However, rDEN3Δ86 and rDEN3-3'D4Δ30 were more than 10-fold restricted in replication compared to wild type DEN3 virus, while the replication of rDEN3Δ30/3 was slightly less than 10-fold restricted. On the basis of this arbitrary cut-off, these three viruses were selected for further evaluation. It is important to note that the rDEN4L\30 virus which has a well-characterized, attenuation and non-reactogenic phenotype in humans was found to be only 6-fold restricted in replication in SCID-HuH-7 mice compared to wild type rDEN4 virus (Hanley et al. 2004 *Vaccine* 22:3440-3448).

TABLE 6

Replication of mutant DEN3 viruses in HuH-7-SCID mice.

| Virus[1] | No. of mice | Mean peak virus titer ($\log_{10}$ pfu/ml ± SE) | Fold-reduction compared to DEN3 (Sleman/78) |
| --- | --- | --- | --- |
| DEN3 (Sleman/78) | 8 | 6.9 ± 0.1 | — |
| rDEN3Δ30/31 | 8 | 6.0 ± 0.3 | 8 |
| rDEN3Δ61 | 9 | 6.3 ± 0.2 | 4 |
| rDEN3Δ80 | 9 | 6.3 ± 0.3 | 4 |
| rDEN3Δ86 | 10 | 5.6 ± 0.4 | 20 |
| rDEN3-3'D4 | 11 | 6.5 ± 0.4 | 3 |
| rDEN3-3'D4Δ30 | 9 | 5.7 ± 0.2 | 16 |

[1]Groups of HuH-7-SCID mice were inoculated into the tumor with 4.0 $\log_{10}$ PFU of the indicated virus. Serum was collected on day 7 and virus titer was determined in Vero cells.

Because the rDEN3-3'D4Δ30 virus and the rDEN3Δ30/31 and rDEN3Δ86 viruses encode the full set of DEN3 structural and non-structural proteins, they would be expected to induce the full complement of humoral and cellular immunity. This more complete immune induction would be advantageous compared to that induced by the chimeric rDEN3/4,Δ30, which encodes only the structural proteins of DEN3.

Replication of DEN3 Mutant Viruses in Tissue Culture

The level of virus replication in Vero cells and mosquito C6/36 cells was assessed for the rDEN3Δ,30/31 and rDEN3Δ86 deletion mutant viruses and the rDEN3-3'D4 viruses with and without Δ30. Replication in Vero cells was analyzed because these cells are the substrate for manufacture, while gowth in C6/36 cells was assessed because attenuation phenotypes in these mosquito cells may be associated with restricted replication in Aedes mosquitoes which serve as the vector for DEN virus transmission (Hanley et al. 2003 *Virology* 312:222-232).

Growth kinetics were evaluated as follows. Confluent monolayers of Vero cells and C6/36 cells in 75 cm$^2$ flasks were infected at a multiplicity of infection of 0.01. Aliquots of 0.5 ml tissue culture supernatant were removed daily for seven days, combined with SPO stabilizer, and frozen at −80° C. Virus titer of all samples was determined by plaque assay in Vero cells. The limit of detection for the plaque assay is 1.0 $\log_{10}$PFU/ml.

Figure 19:
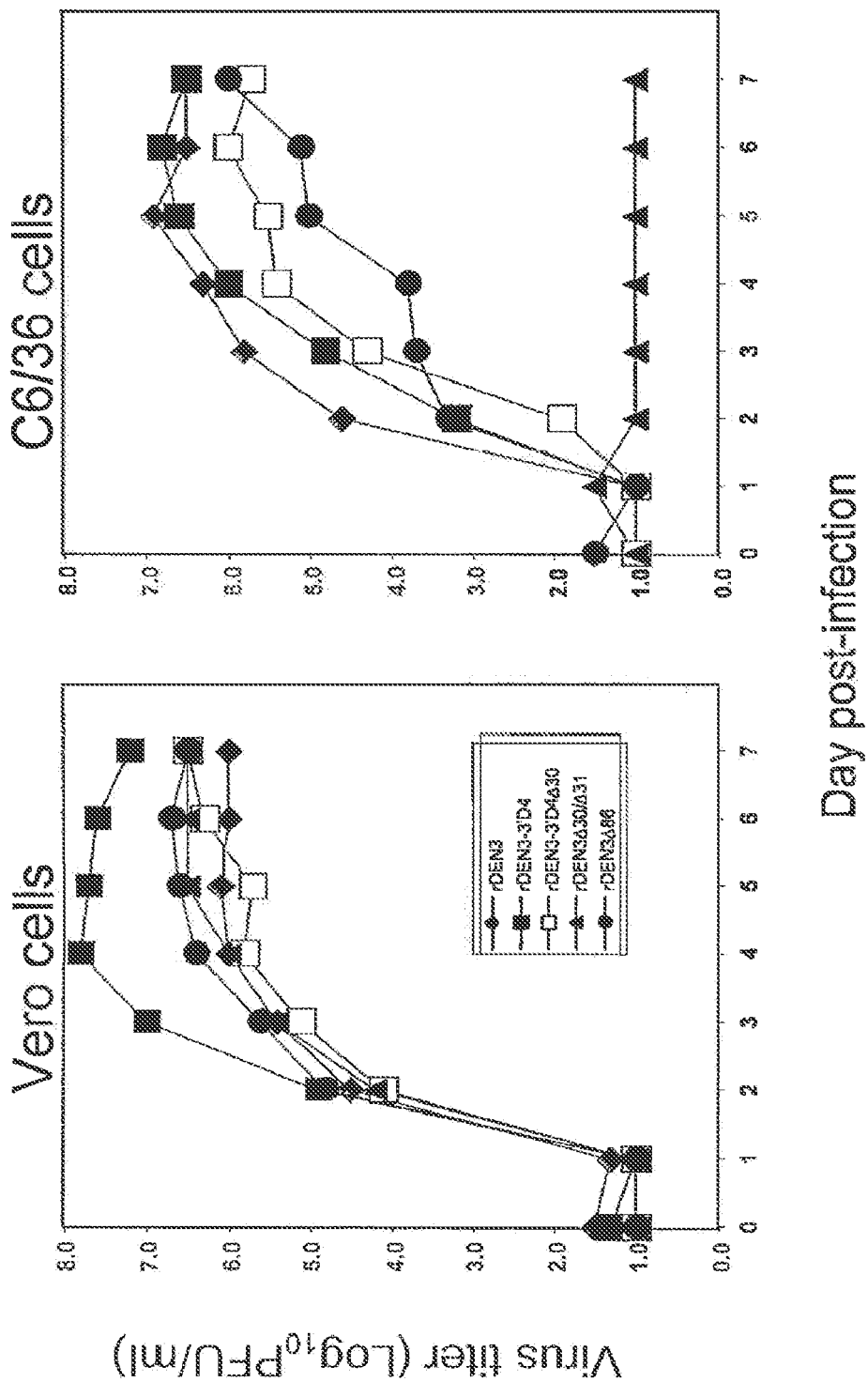
FIG. 19. Replication in vero cells and C6/36 cells. Four mutant viruses were compared to wild type rDEN3 for replication in vero cells and C6/36 cells. 75 cm 2 flasks of confluent cells were infected at a multiplicity of infection of 0.01. Aliquots of 0.5 ml were removed from flasks daily for seven days. After addition of spg to a concentration of 1×, samples were frozen on dry ice and stored at −80° C. Virus titer was determined by plaque assay on veru cells for all samples. The limit of detection is 1.0 $\log_{10}$pfu/ml.

The replication kinetics of each virus in both cell lines is shown in FIG. 19. In Vero cells, iDEN3Δ30/31, rDEN3Δ86, and rDEN3-3'D4Δ30 replicated to a peak level that approximated that of wild type rDEN3 and with similar kinetics to that of wild type rDEN3. These three vaccine components reached peak virus titers of 6.5 to 6.7 $\log_{10}$ PFU/ml which demonstrates the feasibility of manufacture for each of these viruses. In Vero cells, the rDEN3-3'D4 virus replicated to a peak titer of 7,8 logioPFLUml which is nearly 100-fold higher than that observed for wild type rDEN3 indicating that inclusion of the DEN4 3"-UTR may augment replication in Vero cells. This could also be attributed to more efficient Vero cell adaptation of the rDEN3-3'D4 virus. rDEN4 replicates to a peak titer of approximately 8.0 $\log_{10}$PFU/ml which indicates that the chimeric virus achieves a peak titer that does not exceed that of either of its parent viruses (Blaney J E et al. 2006 *Viral Immunol.* 19:10-32).

Analysis of virus replication in C6/36 cells demonstrated that rDEN3Δ86 and rDEN3-3'D4Δ30 reached peak titers approximately 10-fold lower than the peak virus titer of wild type rDEN3 virus, 6.9 $\log_{10}$PFU/ml (FIG. 19). The rDEN3-3'D4 virus replicated to a peak titer similar to that observed for wild type rDEN3. The most striking result was the lack of replication observed in C6/36 cells for the rDEN3Δ30/31 virus. After day 1, virus was not detected in culture medium from C6/36 cells infected with rDEN3Δ30/31 virus despite the efficient replication observed iin Vero cells. These results were confirmed in a second independent growth curve experiment and indicate a host range attenuation phenotype in tissue culture which is envisioned as being accompanied by an attenuation phenotype in mosquitoes as well.

Replication and Immunogenicity of DEN3 Mutant Viruses in Rhesus Monkeys

Based on the slight attenuation in SCID-HUH-7 mice and efficient growth in Vero cells, rDEN3Δ30/31, rDEN3Δ86, and rDEN3-3'D4Δ30 were evaluated in rhesus monkeys. The mutant viruses were compared with wild type DEN3 for level and duration of viremia, neutralizing antibody induction, and the ability to confer protection from wild type DEN3 virus challenge. The rDEN3-3'D4 virus was also evaluated to discern the contribution of the 3'-UTR chimerization upon attenuation with and without the Δ30 mutation. An attenuation phenotype in rhesus monkeys has generally been a strong predictor of safety for vaccine components in clinical trials including rDEN4Δ30, rDEN1Δ30, and rDEN2/4Δ30 (Blaney J E et al. 2006 Viral Immunol, 19:10-32).

Groups of four rhesus monkeys were inoculated subcutaneously with 10 5 PR) of the indicated viruses (Table 7). Two monkeys were mock infected with virus diluent. For detection of viremia, serum was collected on days 0.8 and on day 10 and frozen at −80° C. Virus titer in serum samples was determined by plaque assay in Vero cells. Serum was collected on day 28 for detection of neutralizing antibodies directed against DEN3. Levels of neutralizing antibodies were determined using a plaque reduction neutralization assay in Vero cells against wild type DEN3 virus. On day 35 post-infection, all monkeys were challenged by subcutaneous infection with $10^5$ DEN3 wild type virus. Serum was collected on days 0-8 and on day 10 and frozen at −80° C. Virus titer in serum samples was determined by plaque assay in Vero cells.

Based on the attenuation of rDEN3Δ30/31 in rhesus monkeys and its restricted replication in C6/36 mosquito cells, rDENΔ30/31 was compared to wild type rDEN3 fbr infectivity and level of replication in highly sensitive *Toxorynchites amboinensis* mosquitoes (Table 8). Ten-fold serial dilutions of virus were inoculated intrathoracically, and the

TABLE 7

Replication and immunogenicity of rDEN3 mutant viruses in rhesus monkeys.

| Virus[1] | No. of monkeys | % of monkeys with viremia | no. of viremic days per monkey | Mean peak virus titer[2] ($\log_{10}$ pfu/ml ± SE) | Geometric mean serum neutralizing antibody titer (reciprocal dilution)[3] Day 0 | Day 28 | Post-challenge[4] % of monkeys with viremia | Mean peak virus titer[2] ($\log_{10}$ pfu/ml ± SE) |
|---|---|---|---|---|---|---|---|---|
| DEN3 (Sleman/78) | 4 | 100 | 3.5 | 1.8 ± 0.1 | <5 | 253 | 0 | <1.0 |
| rDEN3Δ30/31 | 4 | 0 | 0 | <1.0 | <5 | 304 | 0 | <1.0 |
| rDEN3Δ86 | 4 | 0 | 0 | <1.0 | <5 | 224 | 0 | <1.0 |
| rDEN3-3'D4 | 4 | 75 | 1.5 | 1.3 ± 0.2 | <5 | 229 | 0 | <1.0 |
| rDEN3-3'D4Δ30 | 4 | 0 | 0 | <1.0 | <5 | 77 | 0 | <1.0 |
| mock infected | 2 | 0 | 0 | <1.0 | <5 | <5 | 100 | 1.8 ± 0.2 |

[1]Groups of rhesus monkeys were inoculated subcutaneously on day 0 with 5.0 $\log_{10}$ PFU of the indicated virus in a 1 ml dose. Serum was collected daily on days 0-8 and 10 and once on day 28.
[2]Virus titer in serum was determined by plaque assay in Vero cells.
[3]Plaque reduction (60%) neutralizing antibody titers were determined using DEN3 (Sleman/78).
[4]Monkeys were challenged after 35 days with DEN3 (Sleman/78) administered subcutaneously in a 1 ml dose containing 5.0 $\log_{10}$ PFU. Serum was collected daily on days 0-8 and 10.

Wild type DEN3 Sleman/78 virus replicated in rhesus monkeys to a mean peak virus titer of 1.8 $\log_{10}$ PFU/ml serum with all monkeys developing viremia (Table 7). These results parallel previous studies of DEN3 in rhesus monkeys (Blaney J E et al. 2004 *Am J Trop Med Hyg* 71:811-821). No viremia was detected in any monkey infected with any of the three vaccine components, rDEN3Δ30/31, rDEN3Δ86, or rDEN3-3'D4Δ30 demonstrating a clear attenuation phenotype for each of these viruses in rhesus monkeys. Interestingly, the rDEN3-3'D4 virus was detected in 75% of monkeys with a mean peak virus titer of 1.3 $\log_{10}$PFU/ml serwn suggesting that the presence of the Δ30 mutation is critical for attenuation of the 3'-UTR chimeric virus. Despite the lack of detectable viremia, mean neutralizing antibody levels in monkeys infected with rDEN3Δ30/31 and rDEN3Δ86 reached levels similar to that of wild type DEN3 virus, 1:253 (Table 7). In contrast, the rDEN3-3'D4Δ30 virus induced mean neutralizing antibody levels approximately three-fold lower than DEN3. However, 100% of monkeys immunized with each vaccine component seroconverted as defined by a four-fold or greater rise in serum neutralizing antibody levels after infection. Thus all monkeys were deemed to be infected by each of the vaccine components despite the lack of detectable viremia. Determination of virus titer in serum after challenge with DEN3 virus indicated that immunization with each of the vaccine components induced complete protection from detectable viremia as would be expected given the observed neutralizing antibody levels.

Replication in Mosquitoes

Replication of rDEN3 and rDEN3Δ30/31 was studied in Toxorynchites' ambainenesis mosquitoes. Intrathoracic inoculation of serial ten-fold dilutions of test virus was performed as described previously (Troyer J. M. e al, 2001 *Am. J. Trap. Med. Hyg.* 65:414-9). After a 14 day incubation, heads were separated and homogenized in diluent. Virus titer in head homogenates was determined by plaque assay in Vero cells.

ability to infect head tissues was evaluated by performing a plaque assay on mosquito head homogenates after a 14 day incubation. The infectivity of rDEN3 and rDENΔ30/31 was very similar as the 50% mosquito infectious dose was approximately $10^{1.3}$ PFU for both viruses (Table 8). However, the level of replication of rDENΔ30/31 in the heads of infected mosquitoes was about 5- to 50-fold reduced. This reduction was significant at the $10^{2.3}$ and $10^{1.3}$ PFU doses tested. This finding indicates that although rDENΔ30/31 has infectivity for *Toxorvnchites* by intrathoracic infection similar to that of wild type rDEN3, there is a statistically significant restriction in the level of replication in mosquitoes afforded by the Δ30/31 mutation.

TABLE 8

Replication of rDEN3 and rDEN3Δ30/31 in *Toxorynchites amboinensis*

| Virus | Dose[a] ($\log_{10}$PFU) | No tested | infected[b] | Mean virus titer[c] ($\log_{10}$PFU/head) | Reduction ($\log_{10}$) compared to same dose of wt virus |
|---|---|---|---|---|---|
| rDEN3 wt | 2.3 | 20 | 90 | 4.2 ± 0.1[d] | |
| | 1.3 | 19 | 53 | 4.2 ± 0.1[e] | |
| | 0.3 | 17 | 18 | 4.3 ± 0.3 | |
| rDEN3Δ30/31 | 2.3 | 12 | 83 | 2.7 ± 0.3[d] | 1.5 |
| | 1.3 | 16 | 44 | 3.1 ± 0.3[e] | 1.1 |
| | 0.3 | 8 | 13 | 3.6 ± 0.0 | 0.7 |

[a]Virus titer administered intrathoracically in a 0.2 µl inoculum.
[b]Percentage of mosquitoes with detectable virus at day 14 post-inoculation was determined by plaque assay on mosquito head homogenates in Vero cells.
[c]Calculated using only values of virus-positive heads.
[d]For $10^{2.3}$ PFU dose of rDEN3 and rDEN3Δ30/31, mean virus titers were significantly different as determined by a Tukey-Kramer post-hoc test (P < 0.001).
[e]For $10^{1.3}$ PFU dose of rDEN3 and rDEN3Δ30/31, mean virus titers were significantly different as determined by a Tukey-Kramer post-hoc test (P < 0.005).

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

We claim:

1. An immunogenic composition that is tetravalent for dengue serotypes 1, 2, 3, and 4, wherein the composition comprises:
   - a nucleic acid encoding a dengue 1 virus comprising a Δ30/31 mutation, wherein the Δ30 mutation deletes nucleotides from about 174 to about 145 of the dengue 1 3' untranslated region (UTR) and the Δ31 mutation deletes nucleotides from about 258 to about 228 of the dengue 1 3' UTR, designated with reverse-order numbering system; and
   - a nucleic acid encoding a dengue 3 virus comprising a Δ30/31 mutation, wherein the Δ30 mutation deletes nucleotides from about 173 to about 143 of the dengue 3 3' UTR and the Δ31 mutation deletes nucleotides from about 258 to about 228 of the dengue 3 3' UTR, designated with reverse-order numbering system.

2. A method of inducing an immune response to a dengue virus in a patient, comprising administering the immunogenic composition of claim 1 to a patient, thereby inducing the immune response.

3. The method of claim 2, wherein the patient is an adult or child at risk of dengue infection or a person infected with dengue virus.

* * * * *